United States Patent [19]
Kodachi et al.

[11] Patent Number: 4,875,990
[45] Date of Patent: Oct. 24, 1989

[54] OXYGEN CONCENTRATION MEASURING DEVICE

[75] Inventors: Toru Kodachi, Nagoya; Jun Usami, Aichi, both of Japan

[73] Assignee: NGK Insulators, Ltd., Nagoya, Japan

[21] Appl. No.: 88,276

[22] Filed: Aug. 24, 1987

[30] Foreign Application Priority Data

| | | |
|---|---|---|
| Aug. 28, 1986 [JP] | Japan | 61-202382 |
| Aug. 28, 1986 [JP] | Japan | 61-202383 |
| Aug. 28, 1986 [JP] | Japan | 61-202384 |
| Sep. 4, 1986 [JP] | Japan | 61-206681 |
| Sep. 4, 1986 [JP] | Japan | 61-206682 |
| Sep. 4, 1986 [JP] | Japan | 61-206683 |
| Sep. 4, 1986 [JP] | Japan | 61-206684 |
| Sep. 4, 1986 [JP] | Japan | 61-206685 |
| Sep. 4, 1986 [JP] | Japan | 61-206687 |

[51] Int. Cl.[4] .................................. G01N 27/46
[52] U.S. Cl. .................. 204/408; 204/425; 204/426; 204/427; 204/428
[58] Field of Search ............ 204/1 S, 421–429, 204/408

[56] References Cited

U.S. PATENT DOCUMENTS

| | | | |
|---|---|---|---|
| 3,546,086 | 12/1970 | Sayles | 204/408 |
| 3,598,711 | 8/1971 | Flais | 204/427 |
| 3,720,594 | 3/1973 | Wilson | 204/427 |
| 4,088,543 | 5/1978 | Ruka | 204/428 |
| 4,098,650 | 7/1978 | Sayles | 204/427 |
| 4,115,235 | 9/1978 | Capone | 204/427 |
| 4,283,261 | 8/1981 | Maurer et al. | 204/408 |
| 4,339,318 | 7/1982 | Tanaka et al. | 204/428 |
| 4,462,246 | 7/1984 | Advani et al. | 204/408 |
| 4,462,891 | 7/1984 | Lawless | 204/426 |
| 4,559,126 | 12/1985 | Mase et al. | 204/425 |
| 4,668,375 | 5/1987 | Kato et al. | 204/425 |

Primary Examiner—T. Tung
Attorney, Agent, or Firm—Arnold, White & Durkee

[57] ABSTRACT

An oxygen concentration measuring device having a very small size detecting portion formed of unitary lamination of plate shaped members of an oxygen sensing element, a heater member and/or a temperature detecting member. The element comprises an oxygen concentration cell and a temperature compensation means for compensating a setting voltage to which an EMF generated by the concentration cell is compared. The detecting portion is provided with a printed contact terminal and housed in a probe equipped with a protecting tube. The printed contact terminal of the detecting portion is arranged to mate with a connecting element housed in a funnel-shaped contact member so as to allow easy mounting and detaching.

15 Claims, 29 Drawing Sheets

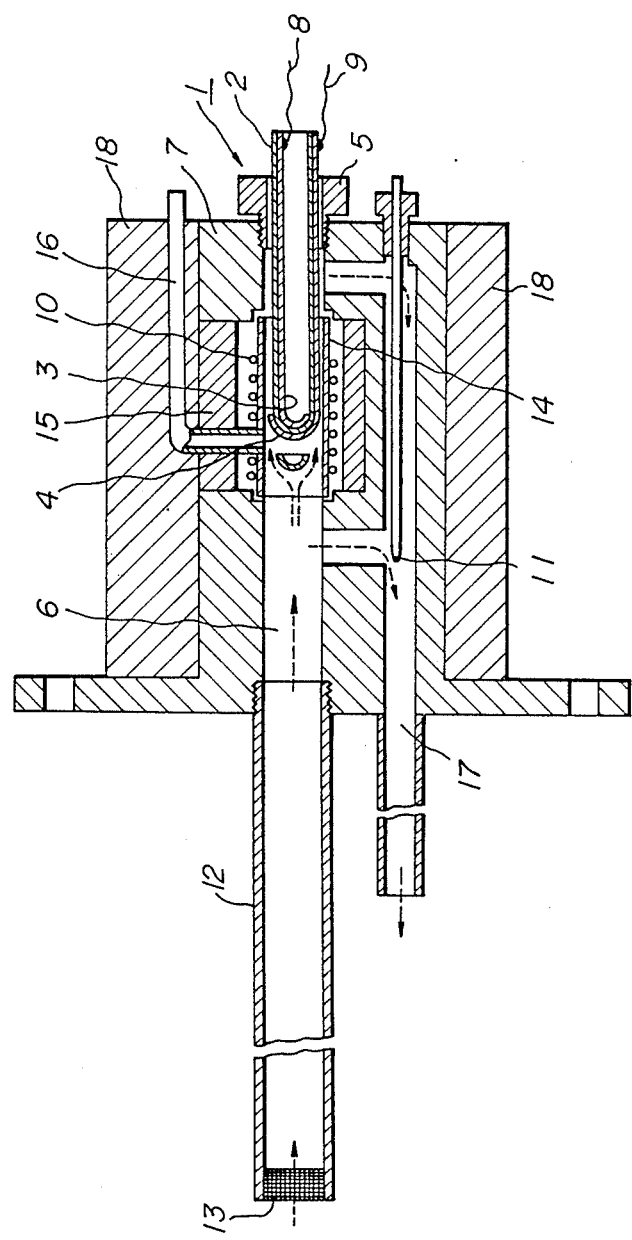
FIG._1
PRIOR ART

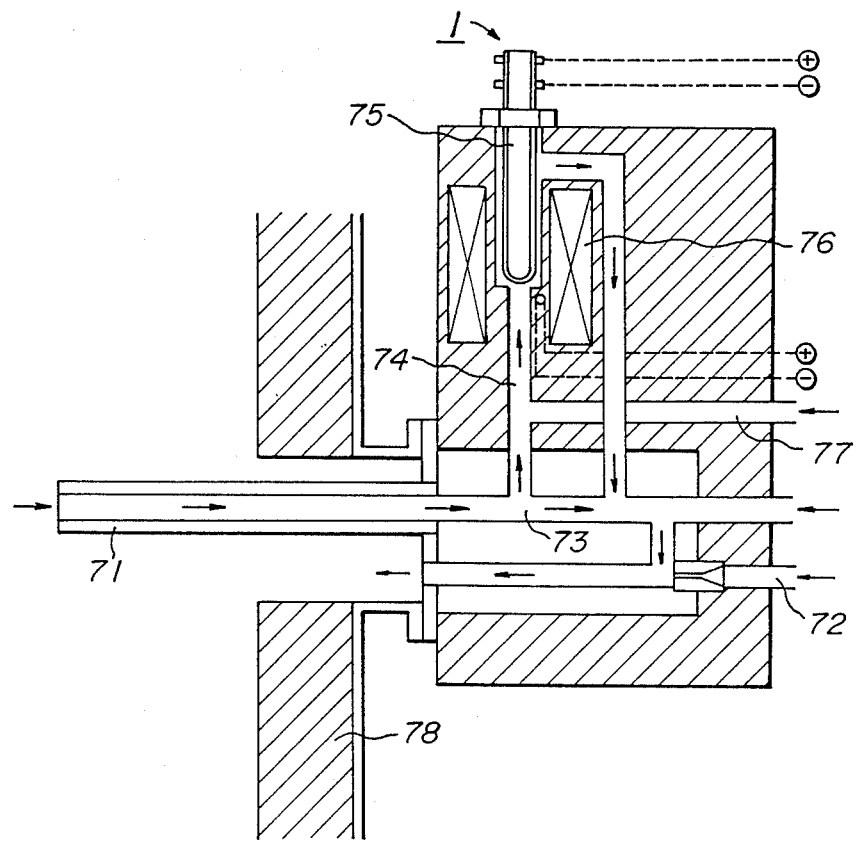
FIG_2
PRIOR ART

FIG_3
PRIOR ART
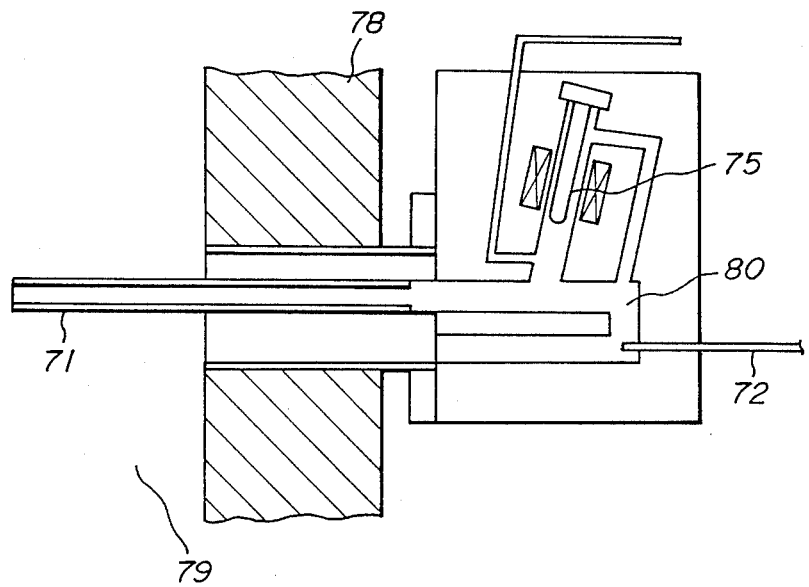
FIG_4
PRIOR ART
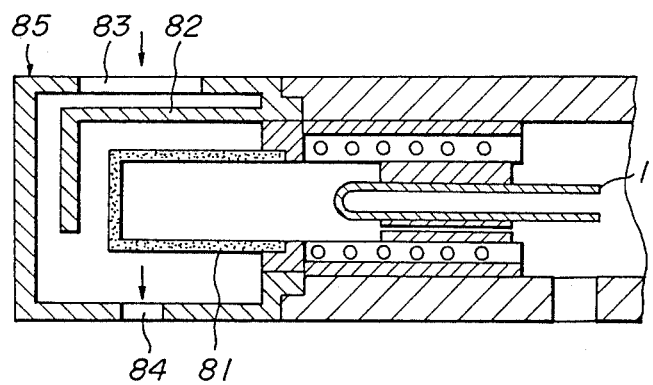

FIG_5
*PRIOR ART*
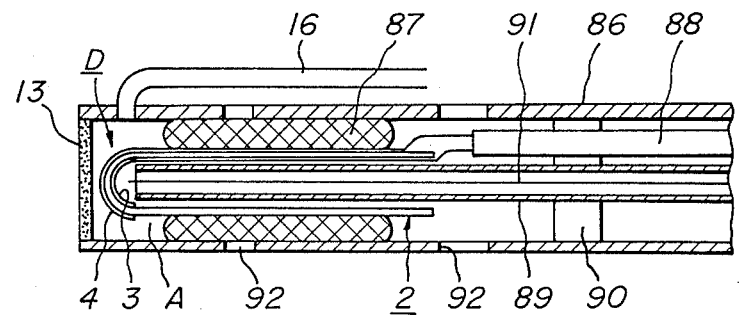
FIG_6
*PRIOR ART*
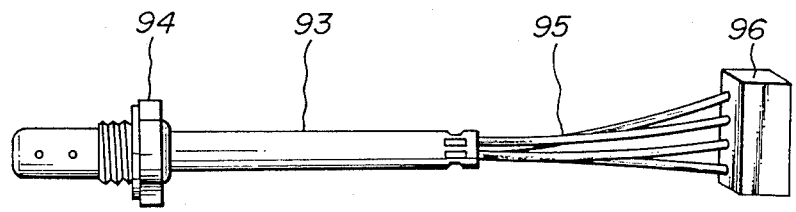

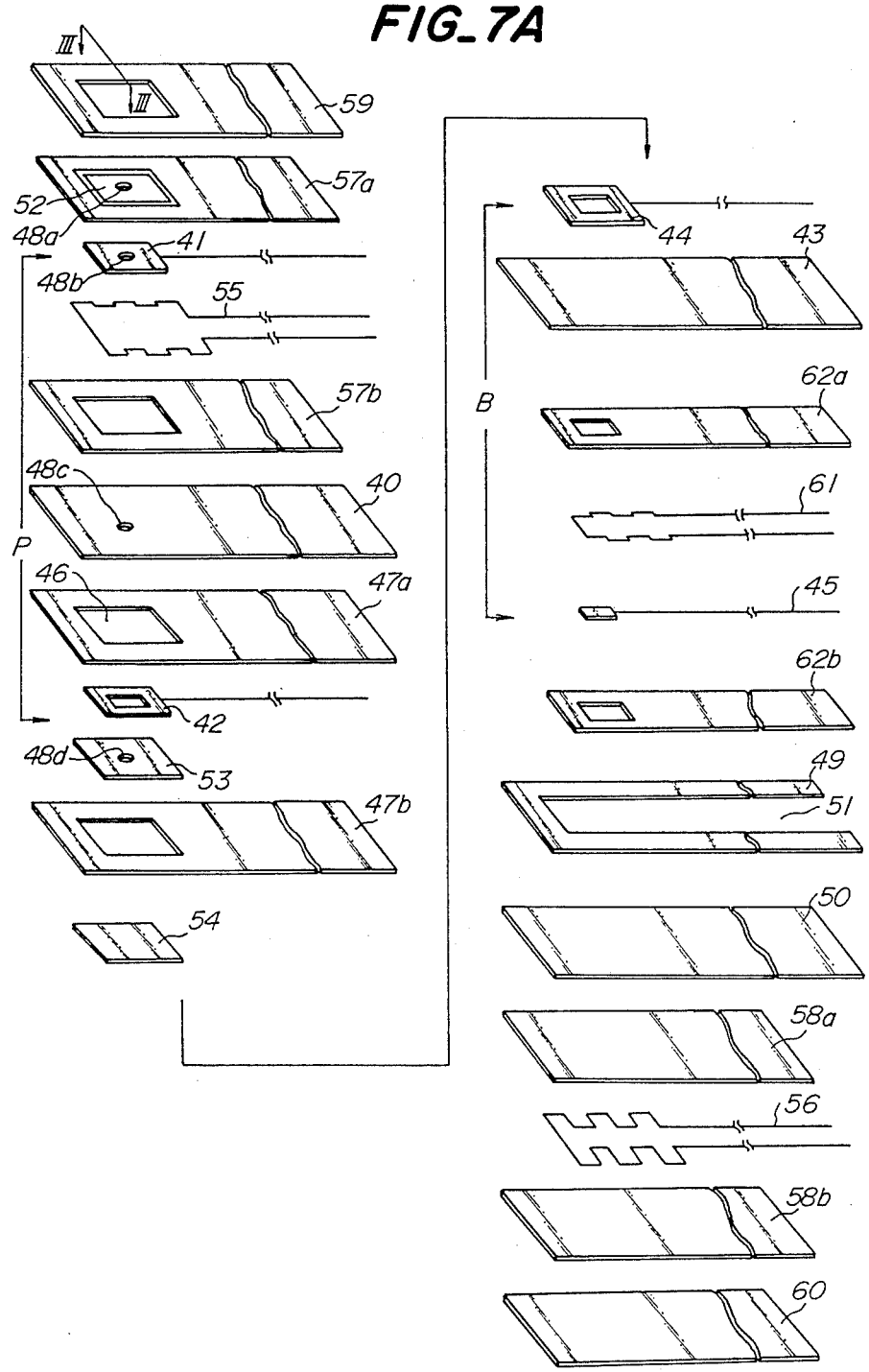
FIG_7A

FIG_8
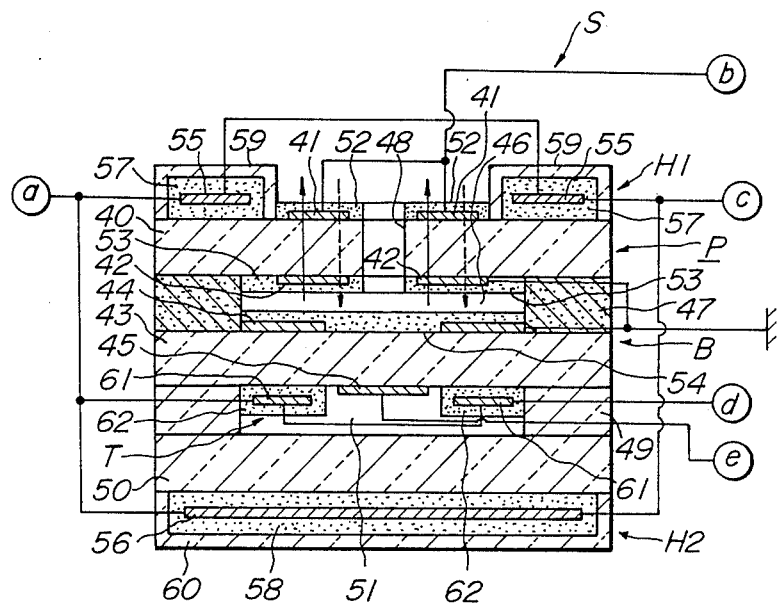

FIG_13
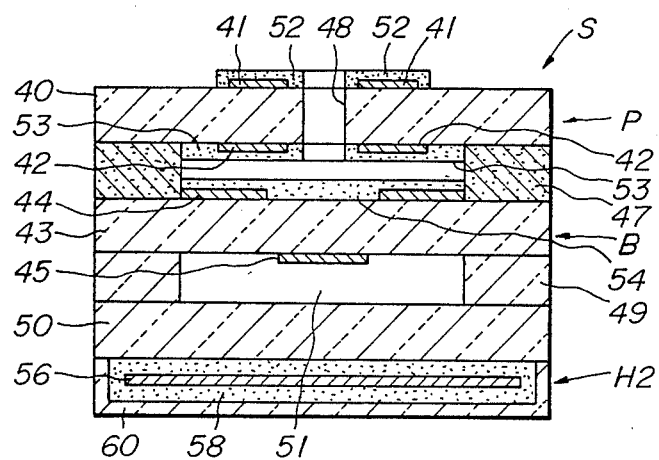

FIG_16
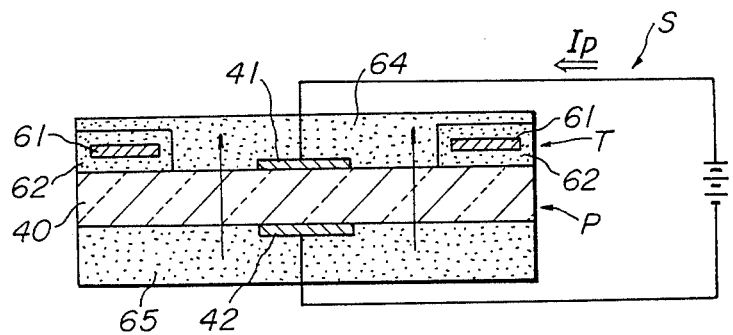
FIG_17
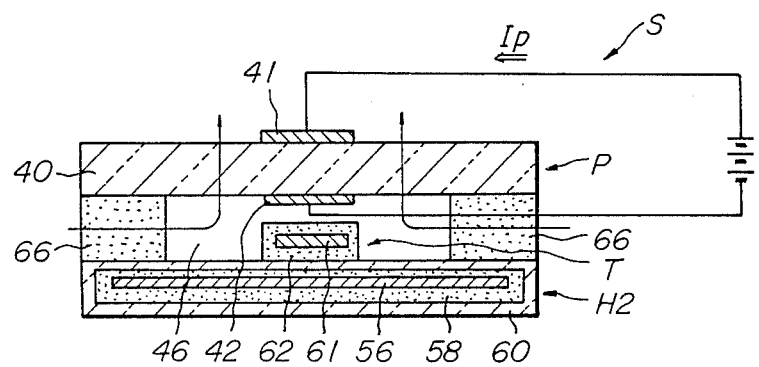

FIG_21
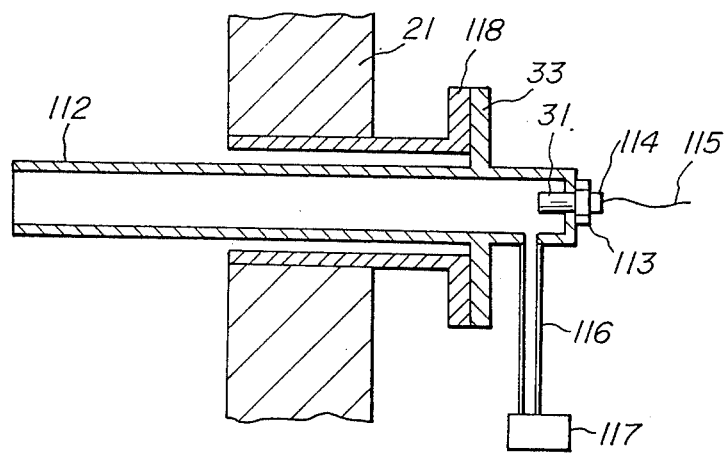
FIG_22
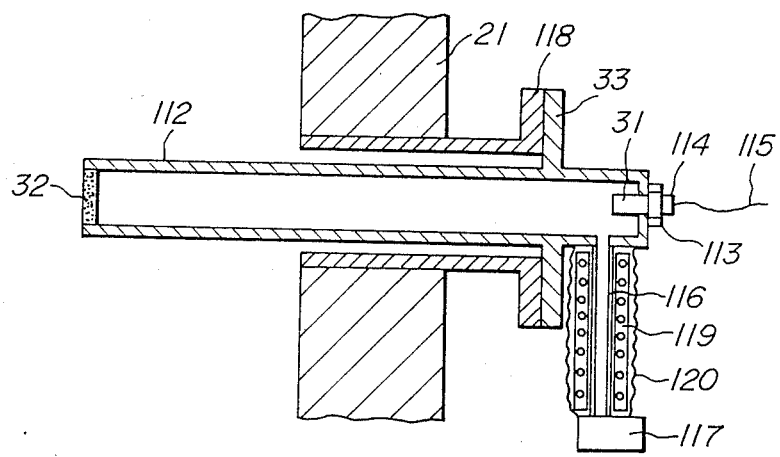

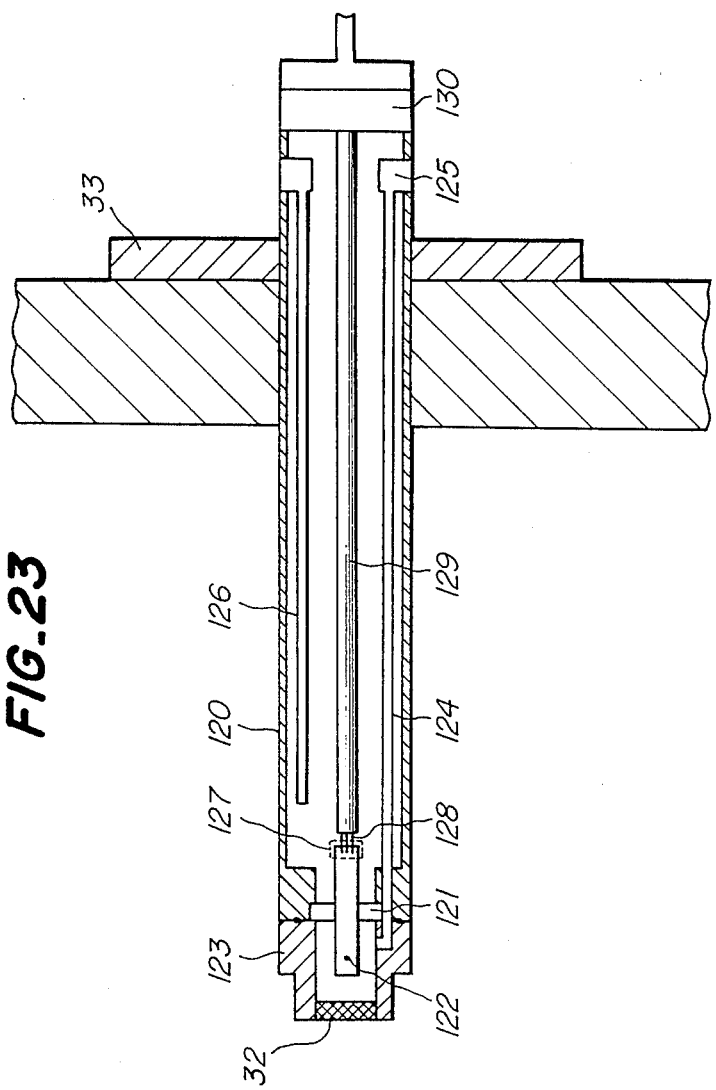

FIG.26A
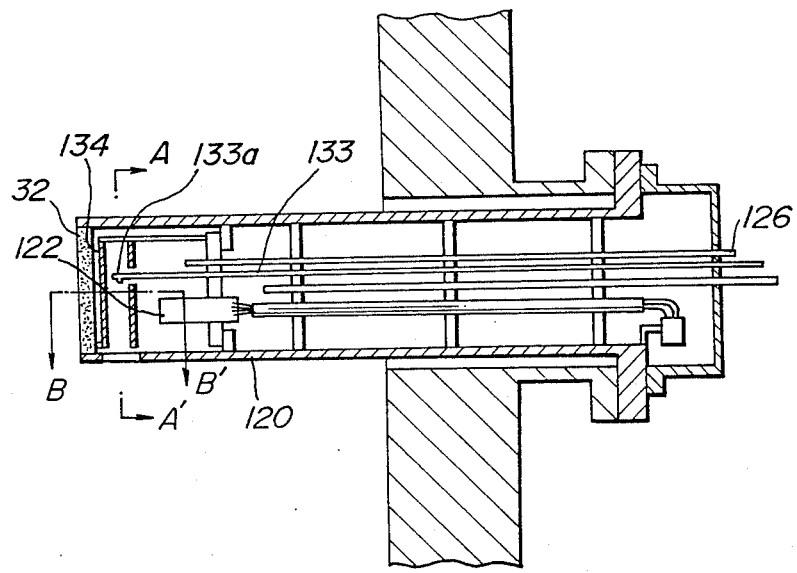
FIG.26B
FIG.26C
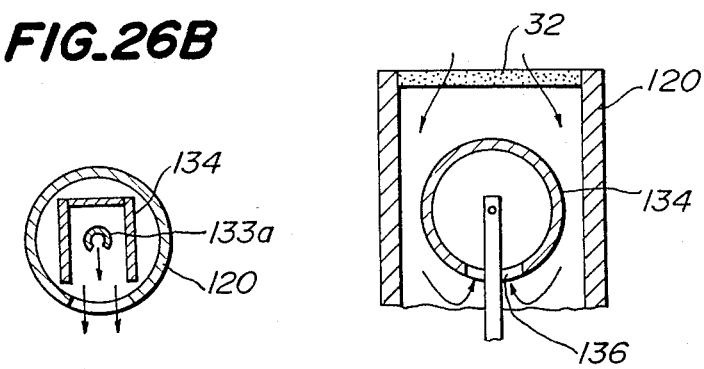

OXYGEN CONCENTRATION MEASURING DEVICE

BACKGROUND OF THE INVENTION 1. (Field of the Invention)

The present invention relates to a device for measuring oxygen concentration in industrial applications purposes. More specifically, the invention relates to an oxygen concentration measuring device suitable for use in the measurement of oxygen concentration in the atmosphere and also for use in the measurement of oxygen concentration in a combustion exhaust gas of an industrial furnace or a boiler by inserting the device into the furnace or in the exhaust gas passageway or affixing it on the wall of the furnace.

2. (Related Art Statement)

A conventional device of this kind has been disclosed in Japanese Patent Application Opened Number 54-99492. In order to help better understand this invention, such a known device will be explained by referring to FIG. 1.

In this measuring device, the sensing cell is formed by an oxygen concentration cell 1. The oxygen concentration cell 1 comprises a closed bottom cylindrical type solid electrolyte element 2, and an inner electrode 3 and an outer electrode 4 provided on the inner and outer surfaces, respectively, of the closed bottom end of the solid electrolyte element 2. Said closed end is placed in a gas passageway 6 by holding the solid electrolyte element 2 by a holder 5 detachably coupled to a frame 7 of the measuring device and an open end of the solid electrolyte element 2 is placed in the open air atmosphere. Lead wires 8 and 9 are coupled to the inner and outer electrodes 3 and 4 to derive out the induced voltage therebetween.

Around the outer surface of the closed end of said solid electrolyte element 2, heater 10 is arranged so as to heat the oxygen concentration cell 1 up to about 500° C.–1000° C. This heater 10 is provided in the gas passageway 6 of the frame 7 in a gas-tight manner. A probe 12 is provided to introduce the combustion exhaust gas to be measured into the gas passageway by suction action of ejector nozzle 11. At the top end of the probe 12, a dust filter 13 is provided. Furthermore, a heater tube 14 mounted with the heater 10 around it is provided and a heat insulating layer 15 is provided to surround the heater tube 14.

An inlet tube 16 of calibration gas is provided and an exhaust passageway 17 and another heat insulating layer 18 are provided.

This known device has disadvantages in that the sensing portion comprising the sensing cell formed of the oxygen concentration cell 1 and a heater member. The heat member has a heater 10 and a heater tube 14 and includes other components of a considerably large size and thus the thermal capacity becomes relatively large. Therefore, a long time is required before the sensing cell of the oxygen concentration cell 1 assumes a predetermined working temperature by the heating of a heat source, for instance by the heater 10. Namely, the warming-up time counted from the start of heating of the heater 10 to the commencement of the actual measurement is very long and furthermore the response speed is slow since the sensing portion is of a large size.

Another oxygen concentration measuring device is known as shown in FIG. 2, which measures the oxygen concentration in an exhaust gas and in which the gas to be measured is introduced in an oxygen concentration detector 1 through an aid of suction of the air ejector 72.

This known oxygen concentration measuring device is of an industrial use and to be used by mounting it on the furnace wall of a combustion furnace etc. and it comprises a main flow tube 73 into which the exhaust gas to be measured for its oxygen concentration and taken by a probe 71 is sucked by suction of an air flow ejected from an air ejector 72, a branch tube 74 through which a branched exhaust gas stream is returned back to the main flow tube 73, an oxygen concentration sensor 75 comprising a closed bottom cylindrical solid electrolyte element 75 detachably mounted at the branch tube 74, a heating furnace 76 fixed near the outer surface of the oxygen concentration sensor 75 and a calibration gas outlet tube 77 connected to a branch tube wall of the gas flow inlet side to the oxygen concentration detector 75.

However, the abovementioned industrial oxygen concentration measuring device has disadvantages also in that the size and weight become large and hence the thermal capacitance increases which results in a long warm-up time due to the fact that the oxygen concentration sensor 75 has a closed bottom cylindrical shape and that the heating furnace 76 is provided separately from the detector 75. Furthermore, as the exhaust gas flows in the branch tube by thermal convection so that the response characteristics are insufficient and the mounting position of the measuring device is limited due to the large-size of the detector.

As an oxygen concentration measuring device using an air ejector, a device having a construction as shown in FIG. 3 is also known, in which the top of the probe 71 is inserted into the exhaust gas passageway 79 from a furnace wall 78, a measuring gas passage 80 is provided at the base portion of the probe 71 and an oxygen sensor 75 having closed bottom cylindrical zirconia electrolyte member and an ejector 72 are provided in this measuring gas passageway.

In the aforementioned industrial gas or oxygen concentration measuring device, as the measuring gas is introduced by a probe 71 into the oxygen sensor 75 there were disadvantages in that the response time varies according to the variation of flow rate of the measuring gas and that the time required for the measurement is long.

Furthermore, as the measuring gas passageway 80 and the oxygen sensor 75 are provided outside of the furnace wall 78, which has a relatively low temperature, the temperature of the measuring gas sucked by the ejection stream of the ejector 72 becomes low. This causes condensation of water ($H_2O$) content and acid ($SO_x$ for instance $SO_2$ etc) content included in the exhaust gas which causes corrosion of the corresponding parts and also causes blocking of the tube by catching the dust in the exhaust gas.

A further industrial oxygen concentration measuring device for measuring the oxygen concentration in an exhaust gas collected by a probe by using a solid electrolyte element, is disclosed in Japanese patent application opened specification No. 56-69553. Namely, such a device is as shown in FIG. 4. This oxygen concentration measuring device comprises an oxygen concentration sensing element 1 formed of a closed bottom cylindrical solid electrolyte element combined with a gas collector 85 having a gas flow inlet 83 and a gas flow outlet 84 arranged to surround a gas flow buffer plate 82 provided at an entrance side of a filter 81, which is also arranged to surround said closed end of the solid electrolyte element.

However, the abovementioned oxygen concentration detector uses a Nichrome wire heater and a closed bottom oxygen sensing element so that about 50 mm diameter is required for the probe and the overall device size becomes large and thus the weight becomes heavy. Additionally, this detector also has inconveniences in that the response time is considerably long and the applicable temperature range and range of measuring concentration are narrow.

In the known oxygen concentration measuring device for detecting oxygen concentration in the exhaust gas of a boiler of a steam power station or various combustion furnaces, it is the usual practice to form the measuring devices separately for the high temperature purpose and for the low temperature purpose making about 600° C. as the boundary therebetween.

In the measuring device for the high temperature purpose to be used for temperature higher than about 600° C., as the temperature is already in the working temperature or above it, a temperature measuring element for measuring the temperature of the oxygen sensor element in the proximity of the sensing element and the electromotive force of the oxygen sensing element at each measuring temperature is calibrated at first and then it is derived as an output signal.

In the measuring device to be used at a temperature equal to or lower than about 600° C. to the room temperature, as the above temperature is, in general, lower than the working temperature of the oxygen sensing element, the temperature in the proximity of the oxygen sensing element is adjusted by a heater to be above the working temperature, and the electromotive force E corresponding to the oxygen partial pressure in the measuring gas is processed by an exponential logarithmic conversion circuit in the analysis unit and the oxygen concentration is derived at the output as a directly readable value.

In these kind of the known oxygen concentration measuring devices having separate arrangements for high temperature use and for low temperature use, it was very troublesome to exchange the above two kinds of measuring devices to meet the respective measuring temperature range when the oxygen concentration is to be measured in an atmosphere varying its temperature from room temperature to about 1400° C.

In the above kinds of known measuring devices, a small measuring chamber is arranged for mounting the probe for collecting the measuring gas. The construction of such a measuring chamber will be explained by referring to FIG. 5.

The closed bottom cylindrical solid electrolyte element 2 is provided with an inner and outer electrodes 3, 4 which are formed by coating precious metal such as platinum on both inner and outer surfaces of said solid electrolyte element and firing said coating layers. The solid electrolyte element 2 with electrode layers 3, 4 are housed in a metal cylindrical tube 86 being supported to keep the position in the cylinder by closely stuffing ceramic fibers 87 made of metal oxide fibers such as alumina, silica, etc. A lead wire protecting tube 88 is provided to passing the lead wires to the inner an outer electrodes 3 and 4 for protection.

A reference or standard air inlet tube 89 for introducing the reference air, for instance the atmospheric air, is provided at inner side of the closed bottom cylinder of the solid electrolyte element 2. The reference air inlet tube is supported by a fixing member 90. In the reference air inlet tube 89 a temperature measuring element 91 for instance formed as a platinum and platinum-rhodium thermocouple is inserted to measure the temperature of the solid electrolyte element.

At an open end of said metal cylindrical tube 86, a ceramic filter 13 is provided allowing to pass the measuring gas by diffusion. A calibration gas inlet tube 16 for introducing said reference or calibration gas to contact with the outer electrode 72 of the solid electrolyte element 71 and an exhaust outlet 92 for exhausting the measuring and the calibration gases are provided on the cylindrical tube 86.

This device has also disadvantages in that the closed bottom cylindrical solid electrolyte element 2 for calibrating the sensing portion becomes a large size especially due to a large size of the oxygen sensing portion at the closed bottom from the construction. For the above reason, it has been very difficult or almost impossible to minimize the size of the small measuring chamber A housing the oxygen sensing portion D and being bounded by said cylindrical tube 86 and the ceramic fiber filter 87 to be smaller than a certain limit.

For this reason, for the calibration of the device, a comparatively large amount of the calibration gas should be introduced into the small measuring chamber A and also as the supply time thereof is long and thus the calibration requires a comparatively long time. This causes a problem in that the calibration is not carried out in a simple manner during the measurement.

In the abovementioned known oxygen concentration measuring devices, it was necessary to derive the electric signal generated in the oxygen detecting element out of the furnace. For this purpose, auxiliary lead wires for connecting the oxygen sensing element to the outside lead wires are provided in the probe.

One example of the lead wire mounting structure is shown in FIG. 6. This lead wire mounting structure comprises a protecting tube 93 housing the oxygen sensing element inside, a flange 94 mounted on the protecting tube 93, lead wires 95 connected to the connecting terminals provided at the end of oxygen sensing element and for deriving out the output signal from the oxygen sensing element or for supplying control signals thereto, and an intermediate connecting terminals 96 made of plastics for connecting to the lead wires 95.

The electric connection between the oxygen concentration detecting element and the auxiliary lead wires may be acceptable for instance by a connector joint having spring pieces made of phosphor bronze etc. in a low temperature range. However, in a high temperature range, such connecting means using spring contact are quite unsatisfactory since the spring features thereof are deteriorated and may cause bad contact in the electric circuit. For this reason, in the conventional devices used for the high temperature range, the electric contacts of the oxygen detecting element are soldered to platinum lead wires by means of silver solder or platinum solder. This makes the electric connection itself quite satisfactory. But the connecting work is rather troublesome. Furthermore, when the oxygen sensing element is provided at the top of the probe like in the direct insertion system, the exchange of the oxygen sensing element inevitably is accomplished by the exchange of the whole probe and this is uneconomical.

In the device as mentioned above, as the lead wires 95 are exposed to the surroundings at location between the protecting tube 93 and the intermediate connecting terminal 96, there will be a danger of brake down or melting of the lead wires 95 by the contact to other devices such as the combustion furnace due to flexibility of the same.

SUMMARY OF THE INVENTION

The oxygen concentration measuring device according to the present invention has for its object to mitigate the aforementioned drawbacks of the conventional devices and in particular it has an object to realize such a device of small size, light weight and having a simple construction and excellent response characteristics.

Another object of the present invention is to obtain a device of this kind which can effect the measurement over a wider temperature range, for instance, from normal temperature to about 1400° C. and for wider concentration range compared with the conventional devices.

A further object of the present invention is to realize an oxygen concentration measuring device being able to measure the gas content or oxygen concentration of the measuring gas at high speed and stable condition continuously and also able to prevent the condensation of water content or moisture included in the measuring gas.

Still a further object of the present invention is to realize an oxygen concentration measuring device being able to exchange only the detecting portion when the detecting portion becomes deteriorated and thus the detecting portion is mounted in an easily detachable manner.

A further object of the present invention is to realize an oxygen concentration measuring device in which the electric connection between the sensing element and the lead wires can be made easily and definitely.

Another object of the present invention is to obtain an oxygen concentration measuring device in which the calibration of the detected output can be effected within a very short time.

The oxygen concentration measuring device according to the present invention has its feature in that it comprises a detecting portion formed of plate shaped unitary laminated members including an oxygen sensing element, a heater member and/or a temperature detecting member.

The oxygen concentration measuring device according to the present invention has its feature in that it comprises a detecting portion formed of plate shaped unitary laminated members including an oxygen sensing element, a heater member and/or a temperature detecting member and that the detecting portion is provided at the base portion or at the top portion of a probe being inserted in the measuring gas at least a part thereof.

The oxygen concentration measuring device according to the present invention has its feature in that it comprises a detecting portion formed of plate shaped unitary laminated members including an oxygen sensing element, a heater member and/or a temperature detecting member, that the detecting portion is arranged in a probe, that an electric contact terminal is provided on the detecting portion by printing, that a contact having heat resistive electric contact elements forming electric contact between the electric contact terminal being inserted therein is provided in the probe, and that a protecting tube accommodating the detecting portion is detachably mounted on the probe so that the detecting portion forms an electric contact in detachable manner with the contact in the probe.

The oxygen concentration measuring device according to the present invention has its feature in that it comprises a detecting portion formed of plate shaped unitary laminated members including an oxygen sensing element, a heater member and/or a temperature detecting member, that a protecting tube for protecting lead wires derived from the detecting portion, and that a connecting terminal holding the outer periphery of the protecting tube and being connected concentrically with the protecting tube and connected to the lead wires is provided.

The oxygen concentration measuring device according to the present invention has its feature in that a small measuring chamber having a filter at inlet portion is provided for accommodating at least an oxygen detecting portion of the detecting portion formed of plate shaped unitary laminated members including an oxygen sensing element, a heater member and/or a temperature detecting member, and a calibration gas introducing a tube is provided for introducing calibration gas into the small measuring chamber, and said small measuring chamber is directly or indirectly mounted in a probe for collecting the measuring gas.

BRIEF DESCRIPTION OF THE DRAWINGS

FIGS. 1 to 5 are cross-sectional views for showing the conventional oxygen concentration measuring device as has been explained;

FIG. 6 is a front view for showing also the conventional device especially for the lead wire portion and this has been explained in the foregoing;

FIGS. 7 to 33 show the embodiments of the oxygen concentration measuring device according to the present invention and in which;

FIGS. 7-A and 7-B are perspective views for showing detecting portion (oxygen sensing element) in exploded view and overall view, respectively;

FIG. 8 is a cross-sectional view taken along line III—III of FIG. 7-A;

FIG. 9 shows the oxygen sensing element shown in FIG. 7-B together with electric controlling circuit in block diagram;

FIG. 10 is a block diagram for explaining the temperature compensation and temperature controlling operation;

FIG. 11 is a block diagram for explaining the operation of a temperature linearizer;

FIGS. 12-A and 12-B are diagrams showing the relation between the temperature and comparison voltage ($V_f$), and between the temperature and oxygen pumping current ($I_p$) and compensation coefficient (K), respectively;

FIGS. 13 to 17 show in cross-sectional views modified embodiments of the oxygen sensing element made according to the present invention;

FIG. 18 shows partly in block diagram the oxygen sensing element shown in FIG. 15 combined with the temperature operational processing circuit;

FIG. 19 shows partly in block diagram the oxygen sensing element shown in FIG. 17 combined with the temperature compensation processing circuit;

FIGS. 20 to 23 are cross-sectional views showing the whole of the oxygen concentration measuring device of the present invention;

FIG. 24 is a modified embodiment of the device shown in FIG. 23 shown in cross-section;

FIGS. 25, 26-A and 27 are cross-sectional views showing the whole of the oxygen concentration measuring device;

FIG. 26-B is a cross-sectional view taken along line A—A' in FIG. 26-A;

FIG. 26-C is a cross-sectional view taken along line B—B' in FIG. 26-A;

FIG. 28 is a cross-sectional view of the oxygen sensing element shown in FIG. 27 showing more details;

FIG. 29 is a cross-sectional view of a modified arrangement of the oxygen concentration measuring device shown in FIG. 27;

FIG. 30 is a cross-sectional view showing essential portion of the oxygen concentration measuring device;

FIG. 31 shows in more detail for the part of FIG. 30;

FIG. 32 is a front view of the oxygen concentration measuring device; and

FIG. 33 is a cross-sectional view of FIG. 32.

DETAILED DESCRIPTION OF THE PREFERRED EMBODIMENTS

In order to clearly explain the concept of the present invention, several preferred embodiments of the invention will now be described in detail by referring to the accompanying drawings.

Figure 7B:
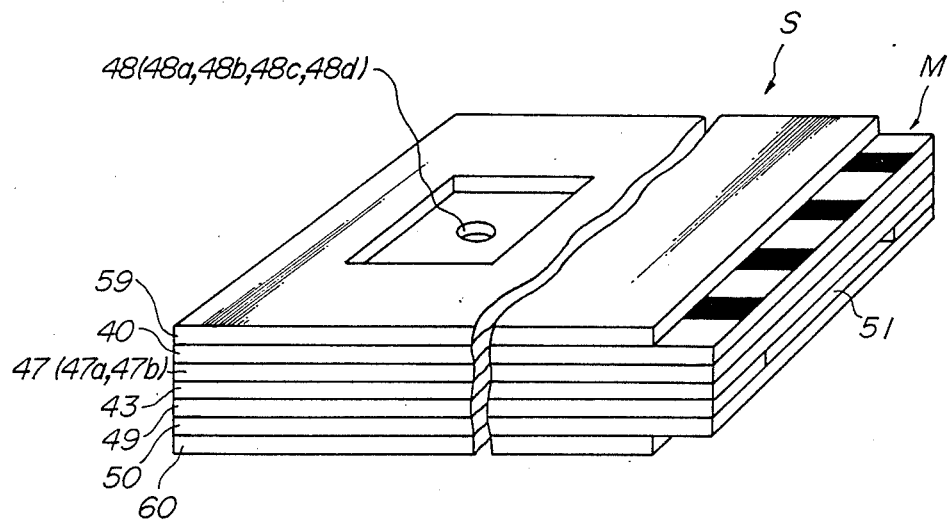

Referring first to FIGS. 7-A, 7-B and 8, an oxygen sensing element S of the oxygen concentration measuring device according to the present invention is shown. The actual size of this oxygen sensing element S is about 5 mm in width, about 1.5 mm in thickness and about 30–60 mm in length. But this value is just to help better understand the present invention and is not intended to limiting the present invention.

At an upper side of this oxygen sensing element S generally shown in FIG. 7-B, there is provided an oxygen pumping portion P comprising a solid electrolyte element 40, and an upper pumping electrode 41 and a lower pumping electrode 42 being arranged at upper and lower sides of this solid electrolyte element 40. Over the upper surface of this oxygen pumping portion P, an upper heater member H1 is provided to surround periphery of the upper pumping electrode 41.

In a similar manner as the abovementioned oxygen pumping portion P, an oxygen concentration cell portion B is provided. This portion B comprises a solid electrolyte member 43 and a measuring electrode 44 and a reference electrode 45 provided at upper and lower sides of the solid electrolyte member 43 respectively.

Between these oxygen pumping portion P and the oxygen concentration cell portion B, a spacer member 47 (47a, 47b) formed of an insulator having a certain thickness is interposed to form a diffusion chamber 46 in the shape of a narrow flat space to which the gas to be measured is introduced with a predetermined diffusion resistance. At the center position of this diffusion chamber 46 in the oxygen pumping portion P, a gas introducing hole 48 (48a, 48b, 48c, 48d) is provided for coupling said diffusion chamber 46 to the outer space, for instance to the measuring location, in which the measuring gas may exist. The measuring gas is introduced through this gas introducing hole 48 (48a, 48b, 48c, 48d) and diffused in the diffusion chamber 46 under a certain diffusion resistance and becomes in contact with the pumping electrode 42 located at lower side of the oxygen pumping portion P. The gas also comes in contact with the measuring electrode 44 of the oxygen concentration cell portion B at the location near said lower pumping electrode 42.

Underneath the oxygen concentration cell portion B, there are provided a spacer member 49 formed of a solid electrolyte and a solid electrolyte member 50 in this order. By this construction, an air passageway 51 is formed in which said reference electrode 45 is exposed. This air passageway 51 communicates with the outer atmosphere at the base portion of the oxygen sensing element S. The abovementioned reference air, in this case the atmospheric air, is introduced in the element through this air passageway 51 and comes in contact with said reference electrode 45.

In the air passageway 51, at a location below the lower surface of the solid electrolyte member 43 and in the proximity of both extremities of the reference electrode 45, a temperature detecting portion T (not shown) is provided.

At a further lower side, a lower heater member H2 is provided. By means of this lower heater member H2, together with the upper heater member H1 arranged at either sides of the oxygen pumping portion P and the oxygen concentration cell portion B, the two portions P and B may be heated up to predetermined temperature (for instance over 600° C.) from both sides in a sandwich like manner.

The solid electrolyte members 40, 43, 50 and the spacer member 49 are made of stabilized or partially stabilized zirconia ceramics which displays oxygen ion conductivity at high temperatures. As is known in the art, this stabilized or partially stabilized zirconia ceramics may be obtained by forming solid solution of zirconium oxide with yttrium oxide or calcium oxide etc. Each of the electrodes 41, 42, 44, 45 is formed of porous platinum etc. Among the electrodes 41, 42, 44, 45, the upper pumping electrode 41, the lower pumping electrode 42 and the measuring electrode 44 being arranged to contact with the measuring gas are applied with porous ceramic layers 52, 53, 54 made of alumina etc. respectively in laminated construction. The measuring gas comes in contact with the electrodes 41, 42, 44 through such porous ceramic layers 52, 53, 54, respectively.

The heater members H1 and H2 are formed of heater elements 55 and 56 being the heating elements covered by porous layers 57 (57a, 57b) and 58 (58a, 58b) respectively formed of alumina etc. having electric insulating feature. Over these porous layers 57 (57a, 57b) and 58 (58a, 58b), air tight layers 59 and 60 are provided respectively formed of solid electrolyte such as zirconia etc. By this, the two heater elements 55 and 56 may be separated or isolated from the outer measuring gas. The heater elements 55 and 56 may be formed, for instance, by printing using paste having the main content of mixture of alumina powder and platinum powder or by arranging cermet like film on the base.

Said temperature detector portion T is constructed by using a resistor body having positive or negative temperature coefficient varying the electric resistance greatly by the temperature variation. A temperature detecting element 61 is embedded in an electric insulative porous layer 62 formed of alumina or the like so that the element 61 is electrically insulated from the surrounding solid electrolyte member 43 and the spacer member 49. The resistive body of this temperature detecting element 61 is formed by laminated printing technics using paste having the main content of powder of zirconia, alumina and the like and platinum powder, or paste having the main content of ceramic powder of ceramic, zirconia, alumina etc. and platinum powder added with about 0.1-0.5% of titanium oxide, or paste having the main content of ceramic powder like cermet, zirconia, or alumina etc. added with oxides of manganese, cobalt, nickel etc., or paste having intentionally high temperature coefficient like cermet. It may also be obtained by arranging cermet like film and the like. The resistive body of the temperature detecting element 61 may be formed by a zirconia porcelain, or a platinum wire or platinum film etc. For forming the laminated print of such platinum wire or platinum thin film, the known techniques of CVD, vapour deposition or sputtering may be used. Instead of using resistive body for the temperature detecting element 61, a combination of different kind of metals or pastes or cermets containing each such different kind of metals can be used to form laminated printed circuit of thermocouple body to be used in the temperature detecting element 61.

The abovementioned oxygen pumping portion P, the oxygen concentration cell portion B, the heater members H1 and H2, the temperature detecting portion T and the spacer member 47 are laminated to form a narrow width plate shaped elongated body and then sintered to form a unitary construction. In FIG. 7-B, M designates a printed electric contact terminal for the pumping electrodes 41 and 42, for the measuring electrode 44, for the reference electrode 45, for the heater elements 55 and 56, and for the temperature detecting element.

In the embodiment as mentioned above, the oxygen pumping portion and the oxygen concentration cell portion form the sensing cell or the oxygen sensing element of the invention, but this may also be formed by either of the two portions.

Furthermore, the heater members may be dispensed with from the oxygen sensing element S, or the temperature detecting member can be dispensed with.

When measuring the oxygen concentration, the oxygen sensing element S or more precisely the oxygen pumping portion P and the oxygen concentration cell portion B are maintained at a predetermined temperature while observing the actual temperature detected by the temperature detecting element 61 of the temperature detecting portion T by conducting a heating current through the heater elements 55 and 56 of the heater portions H1 and H2. In a condition that the oxygen pumping portion P and the oxygen concentration cell portion B are maintained at a certain predetermined temperature for instance, 600° C. or that the predetermined temperature is reached, the measurement process can be started. It takes about 3 minutes in a practical embodiment of the oxygen sensing element S from the beginning of conduction of the heating current to reach the predetermined temperature. The power consumption is about 8 W.

The principle of the oxygen concentration measurement by using the sensing element S will be explained by referring to partial block diagram shown in FIG. 9.

By a comparison of the measuring gas diffused into the diffusion chamber 46 through the gas introducing hole 48 of the oxygen pumping portion P with the reference air in the atmosphere by means of the oxygen concentration cell portion B, an electromotive force E corresponding to the ratio of oxygen partial pressure thereof is produced between the measuring electrode 44 and the reference electrode 45. This produced electromotive force is compared with a comparison voltage $V_f$ (produced electromotive force corresponding to air ratio m≃1). A difference voltage $(E-V_f)$ therebetween is supplied to an oxygen pumping current $(I_p)$ controller 63.

This pumping current $(I_p)$ controller 63 acts to control the oxygen pumping current $(I_p)$ according to the difference voltage $(E-V_f)$, in the following manner.

Figure 9:
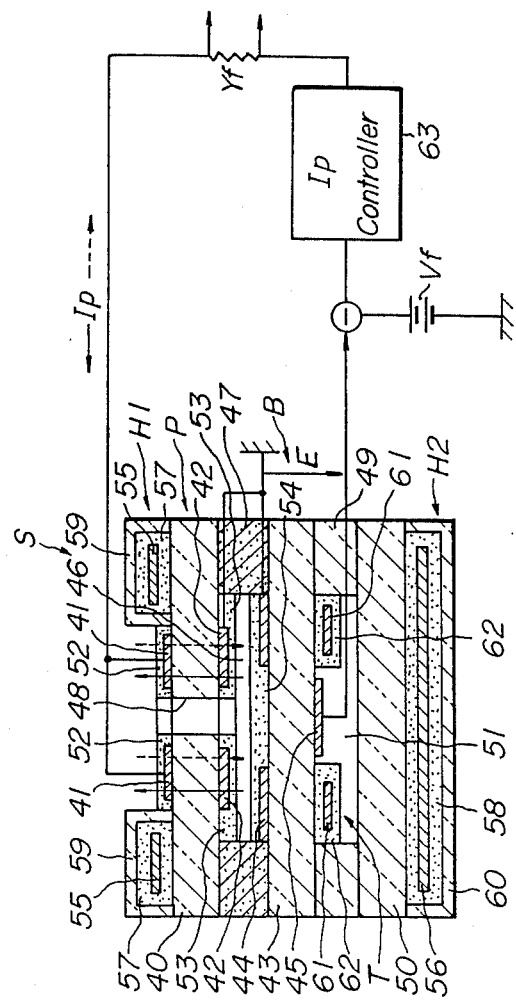

(i) In case of $E < V_f$;

By the regulation of the oxygen pumping current $(I_p)$, the oxygen pumping portion P acts to subtract the oxygen in the diffusion chamber 46 outwardly as shown by the full line shown in FIG. 9.

(ii) In case of $E > V_f$;

By the regulation of the oxygen pumping current $(I_p)$, the oxygen pumping portion P acts to introduce the oxygen into the diffusion chamber by the electrolysis decomposition of the carbon dioxide ($CO_2$) and the water ($H_2O$) content in the measuring gas. (In the diffusion chamber 46, the reaction is as follows:

$$H_2O + \tfrac{1}{2}O_2 \to H_2O,\ CO + \tfrac{1}{2}O_2 \to CO_2$$

By this regulation, the oxygen concentration in the diffusion chamber is controlled to be a predetermined value.

The setting of this predetermined value of the oxygen concentration is so adjusted that the oxygen concentration in the diffusion chamber 46 becomes a value corresponding to air ratio m≃1, or more practically the oxygen concentration becomes 0%.

Each of oxygen molecule, carbon dioxide molecule, hydrogen molecule in the measuring gas has different diffusion coefficient against that of nitrogen so that the oxygen pumping current $(I_p)$ may be expressed by the following equation:

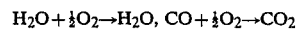

$$I_p = K_1 \cdot P_{O2} - K_2 \cdot P_{CO} - K_3 \cdot P_{H2}$$

wherein, $K_2$ : coefficient in proportion to the diffusion of oxygen molecule.

$K_2$ : coefficient in proportion to the diffusion of carbon monoxide.

$K_3$ : coefficient in proportion to the diffusion of hydrogen.

P : respective partial pressure of oxygen molecule, carbon monoxide molecule, hydrogen molecule.

Accordingly, when the measuring gas is in the oxidation region, as the concentration of carbon monoxide molecule and that of hydrogen molecule are both 0%, the following is obtained.

$$I_p = K_1 \cdot P_{O2}$$

When the measuring gas is in the reducing region, as the concentration of oxygen molecule is 0%, the following is established.

$$I_p = -(K_2 \cdot P_{CO} + K_3 \cdot P_{H2})$$

In summarizing the above explained principle of the measurement of the oxygen concentration, the measurement of the oxygen concentration is carried out to control the oxygen pumping current $(I_p)$ so that the oxygen molecule concentration in the diffusion chamber 46 becomes 0% (air ratio m≃1) and the oxygen pumping current ($I_p$) is measured through a reference resistance ($r_r$).

By this, the oxygen exceeding concentration in the oxidation region and the oxygen shortage concentration in the reducing region can be expressed by a single signal. This will greatly contribute for the formation of a controlling system of atmosphere control of an industrial furnace operating in both the oxidation and reducing regions.

Figure 10:
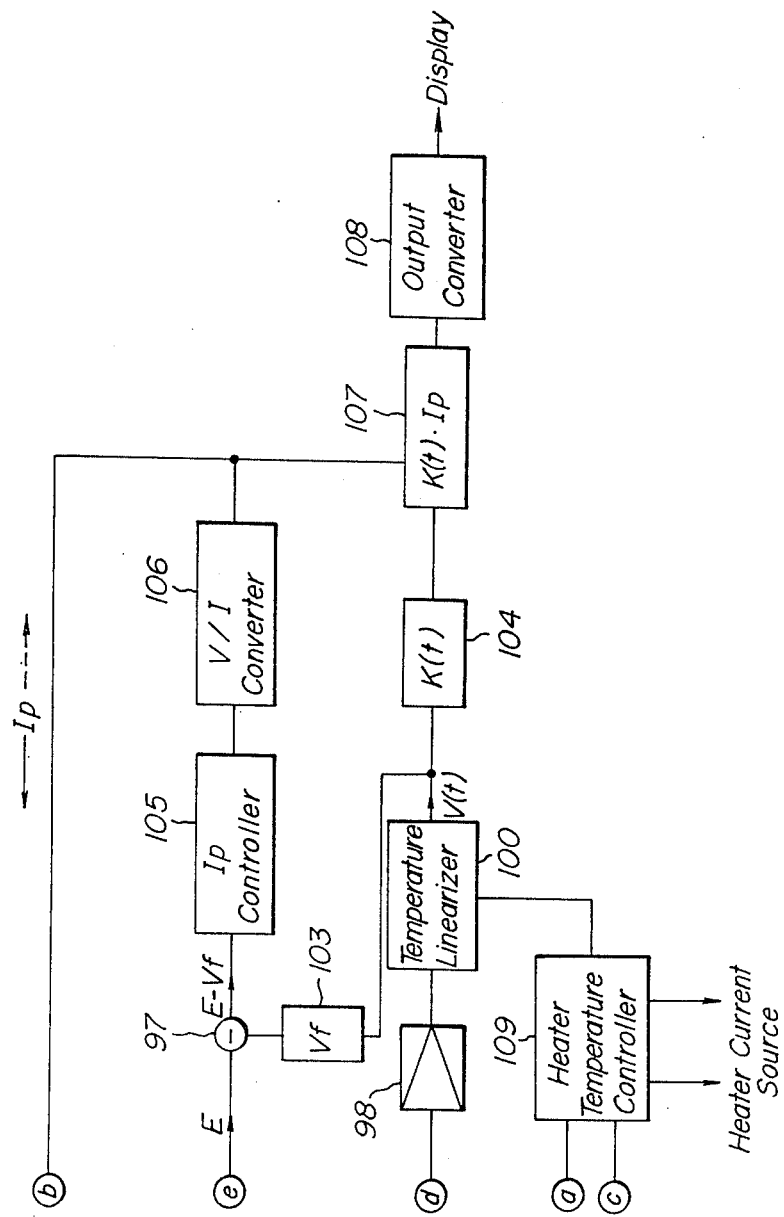

Hereinafter, the principle of compensation of the output of the sensing element S by using the signal of the temperature detecting element will be explained by referring to a block diagram shown in FIG. 10.

The oxygen concentration cell portion B compares the measuring gas diffused into the diffusion chamber 46 through the gas introducing hole 48 of the oxygen pumping portion P with the reference gas of the atmospheric air and an electromotive force E corresponding to the oxygen partial pressure of the two gases is generated between the measuring electrode 44 and the reference electrode 45.

The generated electromotive force E is expressed by the following formula.

$$E = \frac{RT}{nF} \ln\left(\frac{P_A}{P_s}\right)$$

wherein
R: gas constant
T: absolute temperature
n: valency number
F: Faraday's constant
$P_A$: oxygen concentration of reference gas
$P_s$: oxygen concentration of measuring gas In a subtracter 97, this generated electromotive force E is subtracted by a setting voltage $V_f$ (a generated voltage corresponding to air ratio m≃1). The difference voltage ($E-V_f$) therebetween is supplied to oxygen pumping current ($I_p$) controller 63. However, according to the temperature rise, the predetermined value to make the air ratio m≃1, i.e. the setting voltage $V_f$ decreases, for instance, by 0 mV to 100 mV as can be seen from FIG. 12, so that this setting voltage must be compensated in a corresponding value of the temperature variation. For this compensation, the output derived from the temperature detecting portion T is utilized.

When thermistor $T_h$ is used for the temperature detecting portion T, the resistance R of the thermistor has the following feature expressed by the absolute temperature T.

$$R = R_o \exp\left[B\left(\frac{1}{T} - \frac{1}{T_o}\right)\right]$$

The value representing this resistance R obtained by the thermistor $T_h$ is amplified by an amplifier 98 and then supplied to a temperature linearizer 100 connected thereto, in which the temperature-resistance characteristic having logarithmic relation is converted into a temperature-resistance characteristic having linear relationship.

Figure 11:
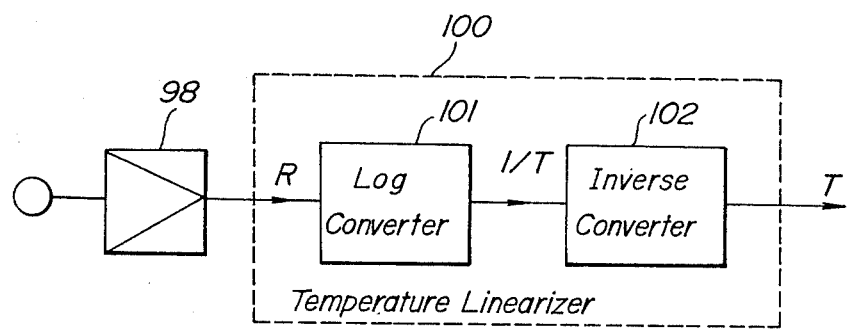

One example of this temperature linearizer 100 will be explained by referring to FIG. 11. The value of the resistance R amplified by the amplifier 98 is converted in the Log converter (logarithmic converter) 101 to have a relation expressed by Log R and 1/T, wherein 1/T=A.Log R+B. (A and B are constants). This Log converter 101 may be formed, for instance, by using the current-voltage characteristics in emitter-base circuit of a transistor, or by using contraction circuit or linear polygonal approximation circuit. From the Log converter 101 a voltage corresponding to the absolute temperature 1/T is obtained and this value is processed in an inverse converter 102 succeeding thereto. This inverse converter 102 is in practice a divider to produce a value in proportion to the absolute temperature T.

The output of the temperature linearizer 100 is on one hand supplied to a reference voltage setting circuit 103 and on the other hand supplied to a coefficient compensating circuit 104 connected to the output.

The reference voltage setting circuit 103 forms a setting voltage $V_f$ corresponding to the variation of the absolute temperature T, for instance, by a function converter based on polygonal approximation and a bias circuit and this setting voltage $V_f$ is supplied to a subtracter 97.

The temperature compensated difference voltage ($E-V_f$) is supplied to the $I_p$ controller 105 and a predetermined control signal for controlling the pumping current ($I_p$) is derived therefrom. This $I_p$ controller 105 delivers predetermined control signals and effects proportion and integration control for the oxygen pumping portion P so that the generated electromotive force of the oxygen pumping portion P becomes equal to the output voltage of the reference voltage setting circuit 103.

The control is for instance as follows.
(i) In case of $E<V_f$,
to control the oxygen pumping portion P to suck off the oxygen in the diffusion chamber 46 outwardly as shown by the full line in FIG. 8.
(ii) In case of $E>V_f$,
to control the oxygen pumping current ($I_p$) to effect electro-decomposition of carbon dioxide ($CO_2$), water content ($H_2O$) in the measuring gas and to introduce oxygen into the diffusion chamber 46 by the oxygen pumping portion P.
(In the diffusion chamber 46, reaction is as follows: $H_2 + \frac{1}{2}O_2 \rightarrow H_2O$, $CO + \frac{1}{2}O_2 \rightarrow CO_2$. By this the oxygen concentration in the diffusion chamber 46 is set to a predetermined value.

In order to control the pumping current ($I_p$) as mentioned above, a voltage to current converter 106 is connected after the $I_p$ controller 105 and the output voltage is converted to the pumping current ($I_p$).

The method of setting the abovementioned predetermined value is to set the oxygen concentration in the diffusion chamber 46 to be an oxygen concentration corresponding to air ratio m≃1 or practically to set the oxygen concentration to be 0%.

In the measuring gas, each of the oxygen molecule, the carbon monoxide molecule, and the hydrogen molecule has different diffusion coefficient against the nitrogen so that the oxygen pumping current ($I_p$) is expressed by the following formula.

$$I_p = K_1 \cdot P_{O2} - K_2 \cdot P_{CO} - K_3 \cdot P_{H2}$$

wherein,
$K_1$: coefficient proportion to diffusion of oxygen molecule
$K_2$: coefficient proportion to diffusion of carbon monoxide molecule $K_3$: coefficient proportion to diffusion of hydrogen molecule P: respective partial pressure of oxygen, carbon monoxide and hydrogen molecule.

Accordingly, when the measuring gas is in the oxidation region, as each of the carbon monoxide molecule and the hydrogen molecule has 0% concentration, the following is given.

$$I_p = K_1 \cdot P_{O2}$$

Furthermore, when the measuring gas is in the reducing region, as the oxygen molecule has 0% concentration, the following is given.

$$I_p = -[K_2 \cdot P_{CO} + K_3 \cdot P_{H2}]$$

The output current of the voltage current converter 106 i.e. the pumping current ($I_p$) is on one hand supplied to the oxygen pumping portion P and on the other hand supplied through a multiplier 107 to an output converter 108.

Figure 12A:
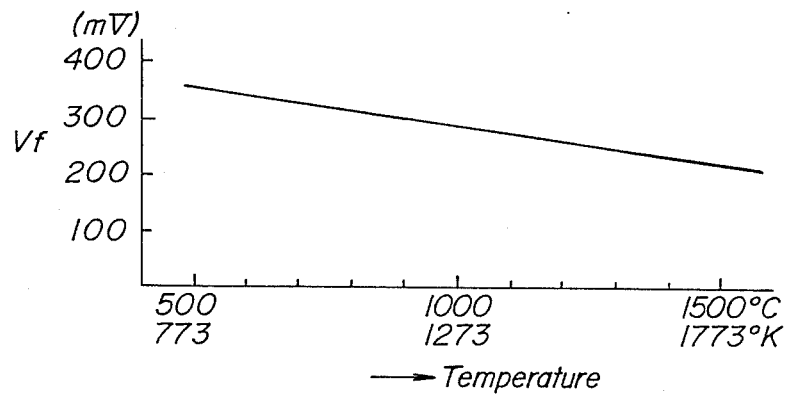
Figure 12B:
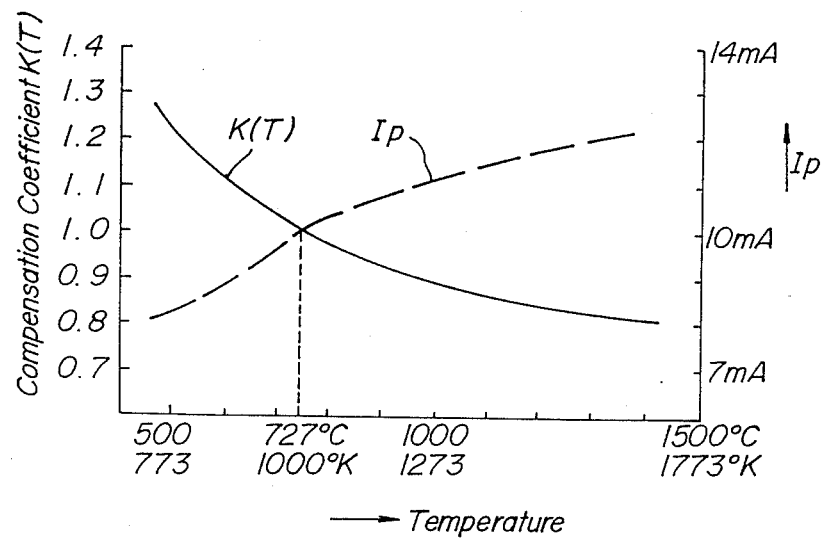

When the oxygen concentration is constant, the pumping current ($I_p$) varies according to the absolute temperature T as can be seen from FIG. 12-B. Therefore, the output voltage of the temperature linearizer 100 corresponding to the absolute temperature is utilized in the coefficient compensating circuit 104, which in practice is a function converter by diagonal approximation and a bias circuit, and a coefficient K(t) as shown in FIG. 12-B, which makes the pumping current ($I_p$) constant against the variation of the absolute temperature T, is derived. In the multiplier 108, the pumping current ($I_p$) is multiplied by thus derived coefficient K(t) so as to obtain a constant pumping current ($I_p$) at a certain oxygen concentration irrespective to the variation of the absolute temperature T.

By the above operation, the pumping current ($I_p$) is derived from the multiplier in 1 to 1 relationship against the oxygen concentration. In the succeeding output converter 108, this value is converted in a desired manner of display mode, for instance, to the oxygen concentration in the measuring gas or a signal representing $O_2$ value—which can show the shortage of oxygen concentration etc.

Now the applicable temperature range from the ordinary room temperature to about 1400° C. is considered. When the temperature of the oxygen sensing element S, or more precisely the temperature of the oxygen pumping portion P and the oxygen concentration cell portion B is below the operational temperature thereof for instance below 600° C., a heater current is conducted to the heater portions H1 and H2 to keep the above portions P and B at a certain predetermined temperature. Even when the oxygen pumping portion P and the oxygen concentration cell portion B become above the operational temperature, the heating of the heating portions H1 and H2 may be continued. It is also possible to interrupt the heating current by a switch in the heater temperature controller 109 when the output voltage of the temperature linearizer 100 reaches above a certain value. In the either cases, since the temperature detection is effected and an operation for the temperature compensation is continuously carried out, a definite oxygen concentration measurement can be effected irrespective to the temperature variation.

Further explanation for the modified embodiments of the oxygen sensing element S will be given hereinafter. The same reference numerals with the aforementioned embodiment show the same parts and duplicated explanation is omitted.

FIG. 13 shows a modified embodiment which is same with the embodiment shown in FIG. 8 except that the upper heater portion H1 and the temperature detecting portion T are removed. In this embodiment, the temperature of the oxygen sensing element S is detected by using the variation of resistance value of the heater element 56 of the lower heater portion H2 and the temperature control is effected. All the other portions are identical with those of the previous embodiment.

Figure 14:
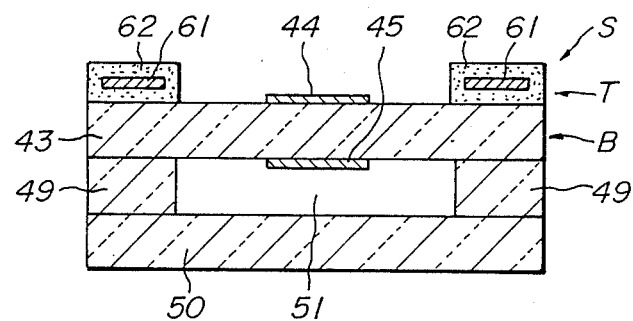

FIG. 14 shows further different embodiment of the invention in which the oxygen sensing element is formed only by the oxygen concentration cell portion B. The temperature detecting portion T is provided on the upper surface of the solid electrolyte member 43. In this embodiment, the oxygen concentration in the measuring gas is measured by the potential difference between the measuring electrode 44 and the reference electrode 45 in the oxygen concentration cell mechanism. Accordingly, as the basic principle, it is not possible to display by a single output signal for the oxygen excess concentration in the oxidation region and the oxygen shortage concentration in the reduction region.

This oxygen sensing element S is so arranged that the element S itself is heated by the high temperature measuring gas and after confirming the fact that the element S is above the predetermined temperature, the measurement is commenced. Accordingly, this embodiment is suitable for use in the measurement of a high temperature measuring gas.

Figure 15:
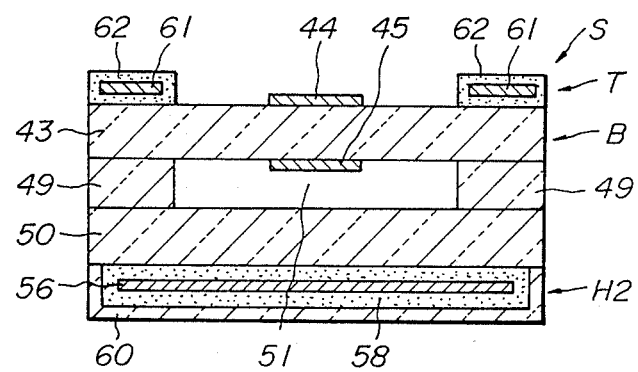

Another modified embodiment shown in FIG. 15 is added with the lower heater portion H2 in the embodiment shown in FIG. 14. This oxygen sensing element S is also same with the previously explained embodiment, namely the element is kept at a predetermined temperature by conducting a heater current for the heater portion H2 depending upon the detected temperature detected by the temperature detecting portion T. Accordingly, this embodiment is suitable for the measurement for the low temperature measuring gas. The other portions are same with the embodiment shown in FIG. 14.

FIG. 16 shows an embodiment, in which the sensing element is formed of the oxygen pumping portion P and the temperature detecting portion T is provided over the upper surface of the solid electrolyte member 40. At upper and lower sides of this solid electrolyte member 40, upper and lower porous ceramic layers 64 and 65 are provided respectively, which are formed of alumina etc. and constitute resistive means for diffusion and the whole members are laminated to form a unitary element. The measuring gas may diffuse into the both porous ceramic layers 64 and 65. In this embodiment, the oxygen concentration is measured by measuring the oxygen pumping current in the oxygen pumping mechanism. Basically, the oxygen excess concentration in the oxidation region and the oxygen shortage concentration in the reducing region can be measured. Since this embodiment comprises only the temperature detecting portion T, it is particularly suitable for use in the measurement of high temperature measuring gas as same as the modified embodiment shown in FIG. 14.

FIG. 17 shows an embodiment in which the oxygen sensing element is formed of the oxygen pumping portion P only like the embodiment shown in FIG. 16. Between this oxygen pumping portion P and the lower heater portion H2, a spacer member 66 formed of alumina etc. is interposed as the diffusion resistive means. The temperature detecting portion T is provided on the upper surface of the lower heater portion H2. The measuring gas is also supplied at the lower surface of the oxygen pumping portion P through the porous spacer member 66. Accordingly, the gas is supplied from both surface sides of the oxygen pumping portion P. Since this modified embodiment comprises the temperature detecting portion T and the lower heater portion H2, it is suitable for use in the measurement of low temperature measuring gas just like the embodiment shown in FIG. 15. The other portions are same as that shown in FIG. 16.

Figure 18:
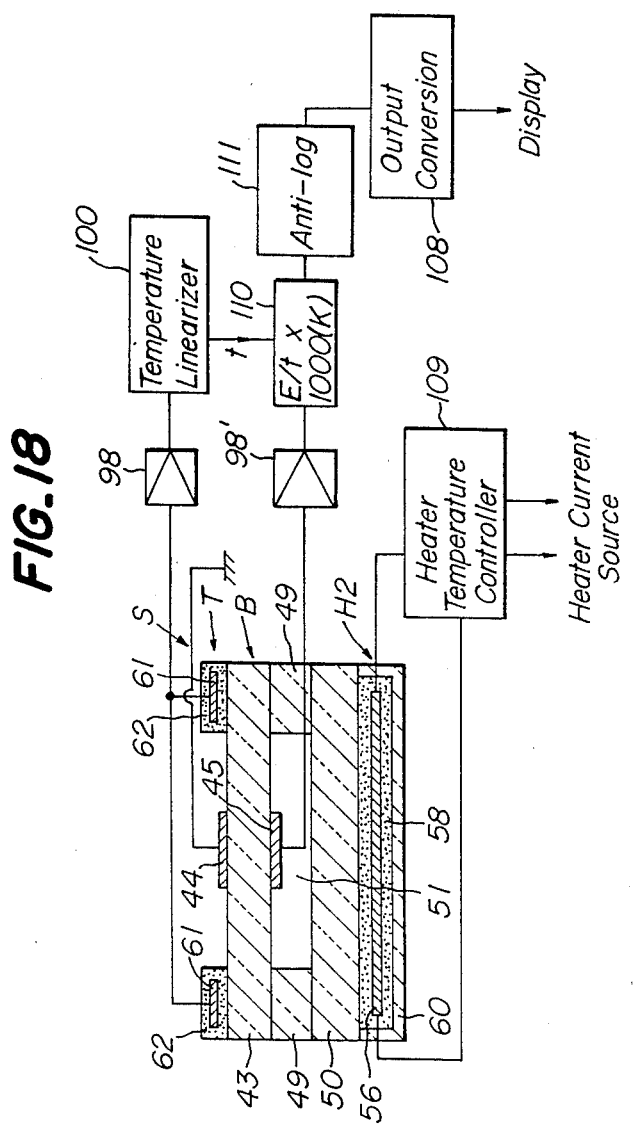

FIG. 18 shows a modification of the oxygen concentration measuring device provided with a temperature operational processing portion. The oxygen sensing element S is the same as explained with referring to FIG. 15, which is provided with the temperature detecting portion T over the upper surface of the solid electrolyte member 43 and a lower heater portion H2 is provided at the lower surface of the solid electrolyte member 50. In this embodiment, the output signal obtained from the temperature detecting portion T is supplied through an amplifier 98 to a temperature linearizer 100 and a voltage V(t) linearly in proportion to the absolute temperature T is obtained at the output as has been explained in the foregoing. This output voltage V(t) is applied to an input of a voltage compensation circuit 110.

In this voltage compensation circuit 110, a voltage E obtained by a measuring electrode 45 through an amplifier 98' is multiplied, for instance by 1000 times, and converted into a generated electromotive force corresponding to that at 1000° (K). Namely, an electromotive force corresponding to the oxygen concentration at an imaginary temperature of 1000° (K.) is obtained therefrom. This means a measurement of the oxygen concentration during a term of imaginary constant temperature.

The output voltage of the voltage compensation circuit 110 is fed to the next stage of an anti-logarithm circuit 111 and processed to evolve the logarithmic function and converted into the oxygen concentration (for instance, into $P_S = P_A e^{-E/K}$) and this will be converted into a desired display value in the succeeding output converter circuit 108.

Figure 19:
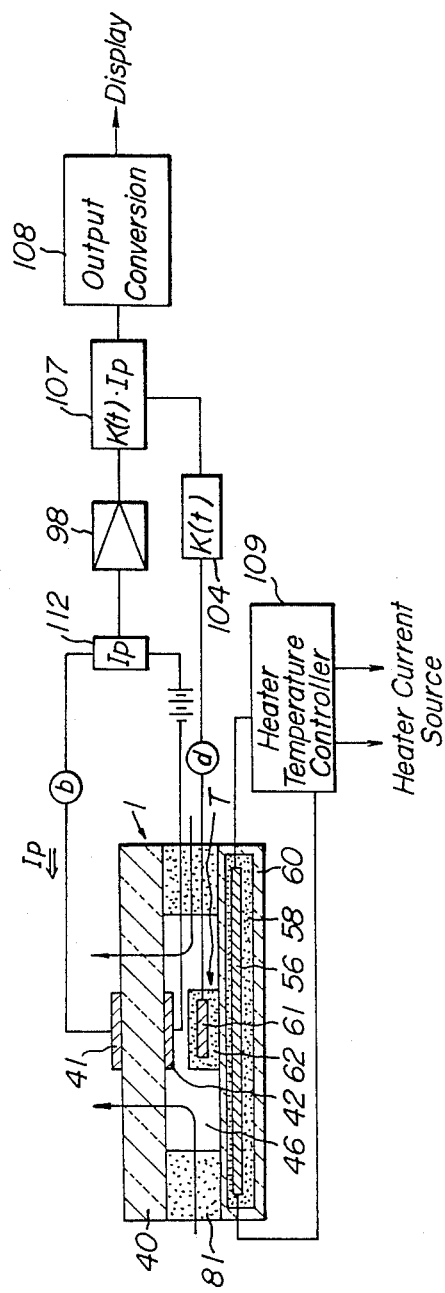

The embodiment shown in FIG. 19 is similar to that shown in FIG. 17 and in the oxygen sensing element, the oxygen sensing cell is formed from the oxygen pumping portion only. Between this oxygen pumping portion P and the lower heater portion H2, a spacer member 81 formed of alumina etc. is interposed as the diffusion resistive means. The temperature detecting portion T is provided over the upper surface of the lower heater portion H2. The measuring gas is also supplied through the porous spacer member 66 to the bottom surface of the oxygen pumping portion P, thus the measuring gas is supplied to both surface sides of the oxygen pumping portion P.

The oxygen sensing element S as constructed in the abovementioned manner, the oxygen concentration is measured by measuring the oxygen pumping current ($I_p$) by the oxygen pumping mechanism. The oxygen pumping current $I_p$ is measured in an electric current meter 112 and the output is supplied to a multiplier 107 through an amplifier 98. The output of the temperature detecting portion T, or more practically the resistance value of the resistor 61 is first converted into a desired function K(t) in a coefficient compensation circuit 104 and then supplied to the multiplier 107. In this multiplier 107, the pumping current $I_p$ is multiplied by the function K(t) and a relation between $I_p$ and oxygen concentration is independently obtained on the temperature range.

Hereinafter, the oxygen concentration measuring device according to the present invention using the above explained oxygen sensing element S will be explained by referring to the accompanying drawings.

Figure 20:
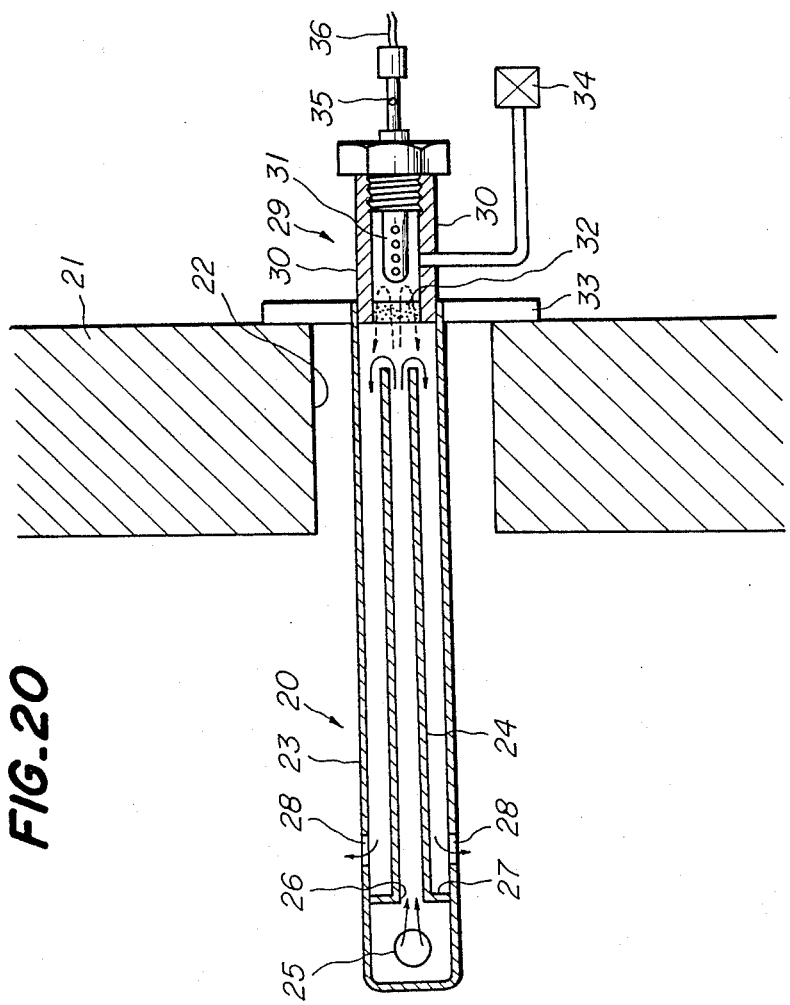

Referring to FIG. 20, a probe 20 for collecting the gas to be measured is arranged by inserting it into an opening 22 provided in the furnace wall of a flue of a combustion furnace. The probe 20 is formed in a double tube construction formed of a closed top outer tube 23 and of an open ended inner tube 24. At the side wall of the top end portion of the outer tube 23, a gas introducing hole 25 is opened to face the combustion exhaust gas (gas to be measured) flowing in the flue or the exhaust gas passageway. Said inner tube 24 is arranged in the outer tube 23 in a position that a top side opening 26 of the inner tube 24 is facing to the gas introducing hole 25. The top open end of the inner tube 24 is supported in the outer tube 23 by means of a partition wall 27 which also acts as a supporter. Thus the inside of the inner tube 24 is separated from the space between the inner tube 24 and the outer tube 23. A gas outlet hole 28 is provided on the outer tube 23 at a location near the partition 27 but locating towards the base side of the outer tube 23 where the inside of the tube shows negative pressure against the combustion exhaust gas (gas to be measured). According to this construction, the combustion exhaust gas in the flue or the gas to be measured (hereinafter simply termed as measuring gas) collected through the gas introducing hole 25 flows as shown by the arrow marks at first the inside space of the inner tube 23 and then through the space formed between the inner tube and the outer tube and finally exhausted through the gas outlet hole 28.

Furthermore, at the base portion of the probe 20, a gas detecting member 29 is connected. This gas detecting member 29 is constituted from a cylinder portion 30 provided to communicate with the probe 20, a detecting portion 31 inserted from the right hand base side of the cylinder portion 30 to project in the inner space thereof and fixed by thread coupling thereto and covered by a protecting cap, and a ceramic filter portion 32 provided at the top of the cylinder portion 30 to supply the flowing measuring gas in the probe 20 to the detecting portion 31 after filtering it. The probe 20 and the gas detecting member 29 are jointly fixed to the furnace wall 21 by a flange 33. A calibration gas supplier 34 is attached on the cylinder portion 30 to supply the calibration gas to the gas detecting member 29. An air hole 35 for supplying the reference air to the detecting portion 31 is also provided and also lead wires 36 are provided to derive the detected signal from the detecting portion 31 outwardly.

FIG. 21 shows an embodiment for the mount of the sensing element according to the present invention. In this embodiment, a plate shaped detecting portion 31 formed by a sensing element and/or temperature detecting member is mounted at the base portion of a probe 112 by means of a supporting member 113 for instance a screw. At an end of the detecting portion not contacting with the measuring gas a connector portion 114 is provided. By connecting this connector portion 114 by a cable 115 to an external power source (not shown), the power is supplied to the pumping portion, to the oxygen concentration cell portion and to the heater element etc. At the base portion of the probe 112 and at the proximity of the detecting portion 31, a measuring gas passageway 116 is provided and a suction member 117 is coupled thereto. For this suction member 117, an ejector or a pump may suitably be used. When carrying out the measurement, the probe 112 is mounted on the furnace wall 21 of a combustion furnace or the like by fixing a flange 33 of the probe 112 to a fixing member 118 jointed with the furnace wall 21.

FIG. 22 shows another embodiment of mounting of the device of the present invention In this embodiment, the same parts already shown in FIG. 21 are shown by the same reference numerals and the explanation is omitted. A difference of this embodiment from that shown in FIG. 21 is the provision of a filter 32 formed of porous ceramics at the top of the probe 112 and the provision of a bandwise heater 119 around the measuring gas passageway 116 covered with heat insulating member 120. The filter 32 has the function to remove the solid content in the measuring gas for instance the dusts and the like. The heater 119 and the heat insulating member 120 are used to keep the temperature in the measuring gas passageway 116 above the dew-point of the measuring gas and by this the corrosion or blocking of the measuring gas passageway is prevented. The heater 119 and the heat insulative member 120 are not always necessary and either one of them may be dispensed with.

An oxygen concentration measuring device shown in FIG. 23 is a so-called direct insertion system of an industrial use. This device comprises a cylindrical probe 120 for collecting the measuring gas and to be inserted into a hole formed in a furnace wall of a flue of a combustion furnace and held its position by a mounting flange 33. This probe 120 is opened at both ends. The material may be metal for low temperature use below 600° C. and alumina for high temperature use over 600° C. At the top end side of the probe 120, a detecting portion 122 is mounted by a cylindrical supporting member 121 made of alumina. The connection between the supporting member 121 and the probe 120 is for instance by shrinkage fitting, mechanical fitting etc. for low temperature use and by fusing by silver solder, platinum solder, or glass etc. for high temperature use. The connection between the detecting portion 122 and the supporting member 121 is made by the same material as mentioned above.

At the top end surface of the probe 120, a filter mounting member 123 is secured by using a heat resistive O-ring or the similar sealing member and at the other end of this filter mounting member 123 a porous ceramic filter 32 for removing dust is secured by means of alumina cement or the like. A calibration gas passageway 124 is arranged to extend from the side wall of the probe 120 at the base portion thereof and through the inner space of the probe 120 and penetrating a thick wall portion at the top portion of the same and also the thick wall portion of the mounting member 123. The calibration gas may be introduced through the calibration gas inlet 125 provided at the end of the calibration gas introducing tube 124 and through the tube 124 to the top portion of the detecting portion 122. By this arrangement, calibration of the detecting portion can be effected.

Furthermore, a reference air introducing tube 126 extending in the inner space of the probe 120 is provided. This tube 126 extends from an inlet provided at opposite side of the calibration gas inlet 125 penetrating the side wall of the probe and passing through the inside of the tube and to terminate its open end near the detecting portion 128 so as to allow continuous supply of the reference air thereto. At the base portion of the detecting portion 128, a terminal portion 127 for connecting lead wires is provided. This terminal portion 127 is connected to a control circuit provided at outside of the furnace through lead wires 128. The terminal portion 127 may have different number of terminals depending upon the construction of the detecting portion. In this example it comprises terminals for the oxygen sensing element, terminals for the heater member, and that for the oxygen pumping portion. The material of the lead wires is platinum when the heat resistivity is required. But in an atmosphere which need not to consider such a strict heat resistivity, other materials may be used. The connection between the terminal portion 127 and the lead wires 128 is sufficiently deformed by physical electrical contact means such as connectors in the low temperature range. But in case of high temperature use, since the physical contact means like connectors may cause bad contact, platinum lead wires 128 must be used by soldering by silver solder, platinum solder or the like. Each of the lead wires is arranged in an alumina tube in order to mutually insulate the lead wires. The lead wires are electrically connected by extending through the alumina tubes to the connector portion at the base of the probe and then connected to an outside controlling circuit (not shown).

Figure 24:
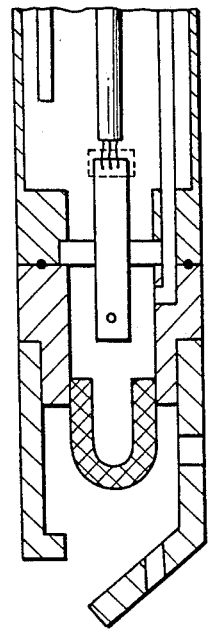

When the dust and soot amount is in an order of a few mg/Nm$^3$ in case of LNG burning or of 200~300 mg/Nm$^3$ in case of C-class heavy oil burning, the known construction shown in FIG. 4 can be used, in which the filter is closed bottom type and a gas collector is mounted about it. However, if the dust and soot amount is larger for instance in an order of 20~50 g/Nm$^3$, a construction shown in FIG. 24 is better to be used. In this case, the oxygen concentration measuring device itself must be arranged perpendicularly against the ground level.

Figure 25:
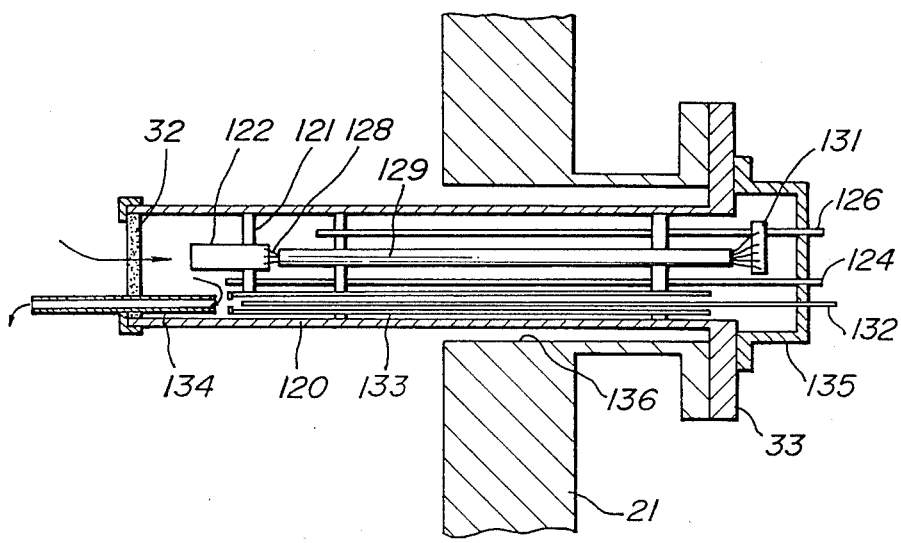

FIG. 25 is a diagram showing one embodiment of the present invention. In this embodiment, the detecting portion 122 is so arranged at top portion of the probe 120 by a supporting member 121 that the top portion of the probe is separated in air tight manner from the base portion thereof. The fixing of the detecting portion 122 on the supporting member 121 is made by fusing by glass, frit etc. or by soldering of silver solder or the like. As for the detecting portion 122, an oxygen sensing element consisting of plate shaped unitary laminated oxygen concentration cell, heater member and/or temperature detecting member is used. At the top end of the probe 120 contacting with the measuring gas, a filter 32 formed of a porous ceramic is provided to remove solid contents like the dust in the measuring gas. At base side end portion of the detecting portion 122, electrodes are provided for connecting the oxygen concentration cell, the pumping portion and the heater member and the like. Platinum lead wires 128 are fixed by soldering with the abovementioned electrodes. The platinum lead wires 128 are mutually insulated by insulating tubes 129 and are connected to a terminal board 131 provided at the base of the probe. At the base portion of the probe 120, a reference air supplying tube 126 for supplying the reference air to a location near the detecting portion 122 and a calibration gas introducing tube 124 having a structure to extend its top end near the top of the probe 120 and for supplying the calibration gas to the top portion of the detecting portion 122 are provided.

In this embodiment, in order to forcedly supply the measuring gas to the detecting portion 122 provided at the top end portion of the probe 120, an ejector pipe 132 is provided to extend in the probe 120 from the outside and through an ejector air supplying tube 133 to supply an ejector air such as atmospheric air to the top portion of the probe 120. In the proximity of the top end portion of the ejector air supplying tube 133 an exhaust tube 134 for the measuring gas is provided to extend to the outside of the filter 32. The measuring gas in the top end portion of the probe 120 is exhausted to outside through the exhaust tube 134 by producing a negative pressure near the inlet portion of the exhaust tube 134 of the measuring gas by supplying the ejector air. The above explained reference air supplying tube 126, calibration gas introducing tube 124, ejector air supplying tube 132 are extending outside through a protecting cover 135 provided at the base of the probe 120 to extend to the relevant outer devices. The lead wires not shown in the drawing connected from the terminal board 131 for instance by a connector are also passing through the protecting cover 135 and coupled to the outside controlling circuit.

The oxygen concentration measuring device as explained above is mounted by a mounting flange 33 provided at the base portion of the probe 120 on to a furnace wall 21 through a hole 136 by inserting the device inside and the oxygen concentration in the exhaust gas is measured. By this arrangement, the detecting portion 122 and the top portion of the ejector air supplying tube 133 and others are exposed to the high temperature and thus in operation these portions may become a temperature above the dew point (at most about 200° C.) of the water or acid content in the exhaust gas so that corrosion or blocking due to condensation of the water or acid content in the exhaust gas can effectively be prevented. In the oxygen concentration measuring device having the aforementioned construction, about 20 l of the measuring gas can be sucked in by supplying about 2 l of the ejector air.

FIG. 26-A is a drawing for showing a different embodiment of the device of the present invention. In this embodiment, the same parts as shown in that in FIG. 25 are shown by the same reference numerals and the duplicated explanation is omitted. The difference of this embodiment from that shown in FIG. 25 is that the manner of introduction of the measuring gas by the ejector air ejected from the ejector air supplying tube 133 only. As can be seen from the A-A cross-section and B-B cross-section thereof shown in FIG. 26-B and 26-C respectively, the measuring gas exhaust tube 134 having an axial slit 136 to allow to insert an air ejecting outlet 133a of the ejector air supplying tube 133 is arranged in parallel with the filter 32. In this construction by supplying the ejector air from the ejector air supplying tube 133, a negative pressure is produced in the measuring gas exhaust tube 134 and thus the measuring gas can be sucked into the space near the detecting portion 122 through the filter 32 and then the measuring gas enters in the exhaust tube through the slit 136 and then exhausted outside.

Figure 27:
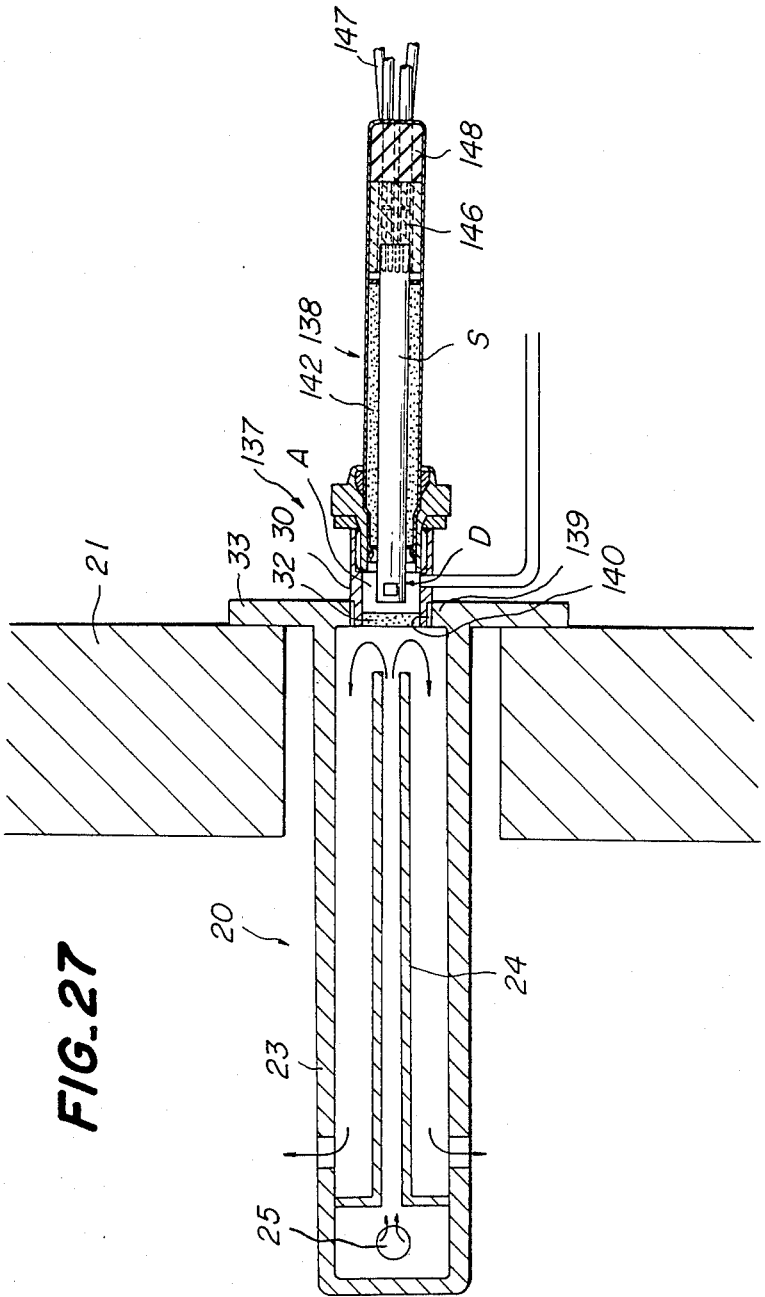

An embodiment shown in FIG. 27 shows a case that the probe 20 shown in FIG. 20 is attached with a different gas detecting member 137.

The gas or oxygen detecting member 137 is formed of an oxygen sensing element 138, a cylindrical tube 30 forming a small measuring chamber A, and a ceramic filter 32 mounted at the top end of the cylindrical tube 30 and located at an inlet portion to said small measuring chamber A. The oxygen sensing element 138 is secured to the base side of the cylindrical tube 30 by threading that the oxygen detecting portion D of the oxygen concentration sensing element S forming the oxygen concentration detecting portion is located in said small measuring chamber A. The oxygen detecting member 137 is mounted on the outer tube 23 of the probe 20 by thread coupling provided in the opening 140 of the base wall 139 and on the outer periphery of the cylindrical tube 30.

Further detailed construction of the oxygen concentration sensing element 138 will be explained by referring to FIG. 28.

An oxygen concentration sensing element S (having size of about 5 mm width×about 1.5 mm thickness×about 30-60 mm length) formed of a narrow width elongated shaped solid electrolyte member having the main content of zirconia is formed with an oxygen concentration detecting portion D at the top thereof. This oxygen concentration sensing element S has the middle portion supported by powder sealing member 142 contained in a metallic cylindrical protecting tube 143 and compressed between two spacer members 141 and 141' and projecting the oxygen concentration detecting portion D outwardly. In a space 144 formed at right hand of the protecting tube 143, an outlet of an air passageway formed in the oxygen concentration sensing element S which will be explained hereinafter is located. In this space 144, a connector 146 is also provided. By which connector 146, an electric connection with the oxygen concentration sensing element S is obtained by inserting its base portion provided with printed electric connecting terminals M, likewisely explained hereinafter. The lead wires 147 extending from the connector 146 pass through a rubber plug 148 fixed by insertion into the right hand end portion in the drawing against said protecting tube 143 and extend to the outside. An air hole 149 is provided on the protecting tube 143 for supplying the reference air to the outlet of the said air passageway 145.

At the left end side of the outer surface of the protecting tube 143, a housing 150 for securing the oxygen concentration sensing element 138 on to the cylindrical tube 30 (FIG. 27) by threading is mounted by mechanical fitting. According to this construction, the protecting tube 143 can be coupled on the cylindrical tube 30 in an air tight manner, while the oxygen detecting portion D of the oxygen sensing element S is inserted in the small measuring chamber A and fixed the location therein. A metal ring 151 and a ring shaped metal packing 152 are provided to keep air tight sealing between the housing 150 and the cylindrical tube 30 and between the protecting tube 143 and the housing 150, respectively.

Figure 28:
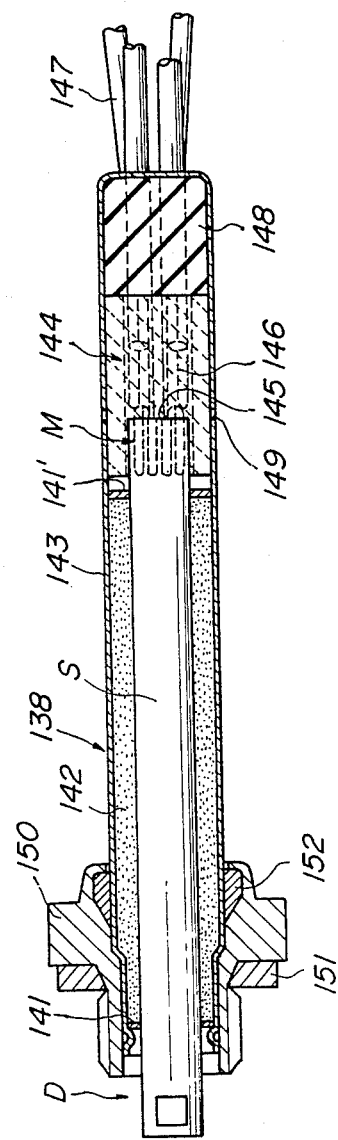
Figure 29:
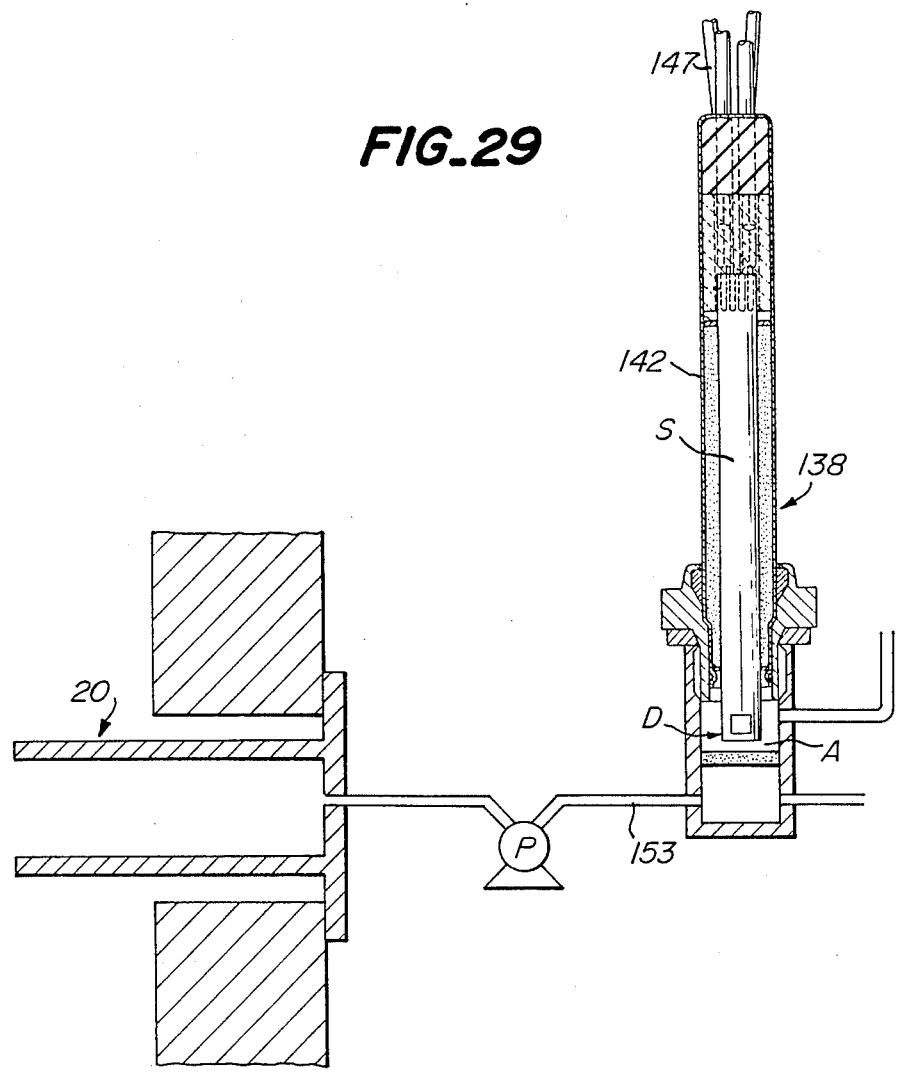

By the embodiment of the present invention shown in FIGS. 27 and 28, the size of the small measuring chamber A can be made about 0.3 cm$^3$ as the oxygen concentration sensing element S constituting the detecting portion is of a very small size as mentioned in the foregoing. In the above embodiment, the oxygen concentration detecting portion D of the oxygen concentration sensing element S is not covered with a protecting cap. But it may be provided when desired. The introduction of the measuring gas into the small measuring chamber A is effected by diffusion. However, a forced supply thereof by an ejector can also be used. Furthermore, the gas measuring device can be mounted indirectly on an introducing tube 153 and the measuring gas can be introduced from the probe 20 by means of a pump P.

Figure 30:
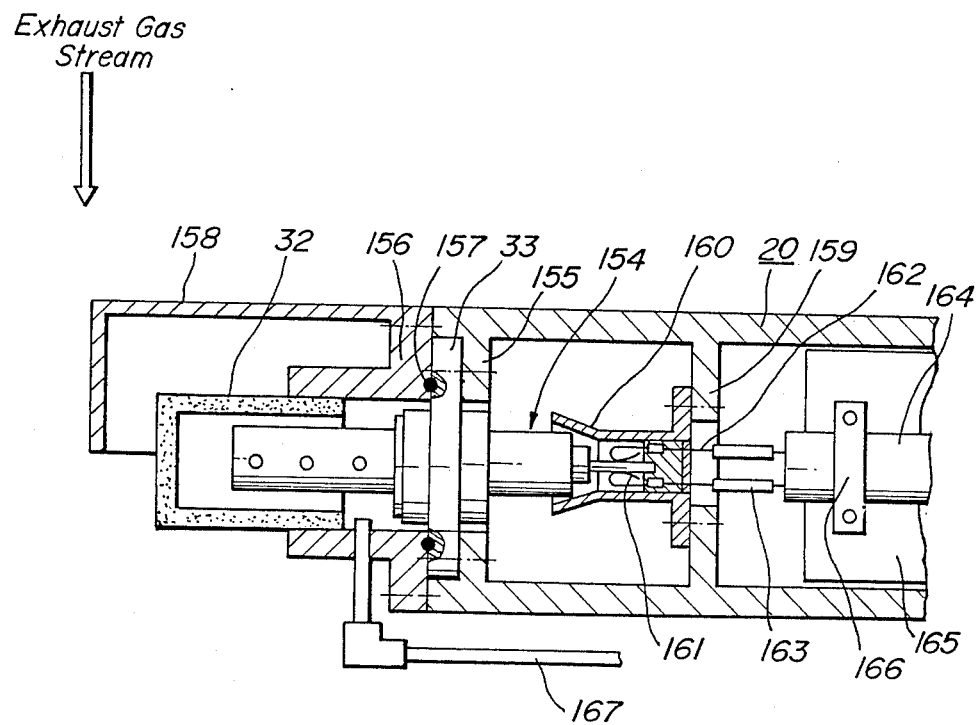

FIG. 30 shows one embodiment of the oxygen concentration measuring device according to the present invention, in which the detecting portion 154 is supported in the probe 20 by fastening a mounting flange 33 against an extended portion 155 of a cylindrical probe 20. The material of the probe 20 is for instance metal or alumina. At the top of the probe 20, an auxiliary mounting member 156 for mounting the filter is detachably mounted by screws with a sealing member, for instance, a metallic 0-ring. At the other end of this auxiliary mounting member 156, a porous ceramic filter 32 for removing dust is attached by means of alumina cement or the like. At outer periphery of thick wall portion of this auxiliary mounting member 156, a gas deflecting plate 158 having half-closed bottom and semi-cylindrical shape is arranged to direct its open mouth towards down stream of the flow of the exhaust gas. By the provision of this gas deflecting plate 158, a direct blow of the exhaust gas to the ceramic filter 32 is prevented and thus the blocking of the filter 32 by the dust or soot is avoided.

In the probe 20, the electric contact terminals M mentioned with respect to FIG. 7-B of the detecting portion 154 are directly inserted into funnel-shaped contact member 160 secured on projections 159 in the probe 20 and the electric connection between heat resistive spring connecting elements 161 provided in the funnel-shaped contact member 160 is established. The connecting elements 161 are connected to lead wires 162 connecting a control circuit (not shown) provided outside. As the material for the lead wires, platinum is preferred in view of its heat resistive feature. The lead wires 162 connecting the contact member 160 to outside through the probe 20 must be mutually insulated. Therefore, in the proximity of the funnel-shaped contact member 160, the lead wires are passed through bead like alumina insulating tubes 163 and derived to outside. The alumina insulating tubes 163 are mounted by means of a mounting metal fitting 166 on a metal plate 165 having the width nearly the same as the inner diameter of the probe 20 and extending therein.

A calibration gas introducing tube 167 is mounted on the side wall of the auxiliary mounting member 156 at the down stream of the flow of the exhaust gas to penetrate the wall. Thus the calibration gas fed through the tube 167 may be supplied to the oxygen concentration detecting portion D of the detecting portion 154. By this arrangement, the variation of the output signal of the detecting portion 154 by the high temperature exhaust gas can be detected and the variation can be compensated electrically by the outer control circuit.

Figure 31:
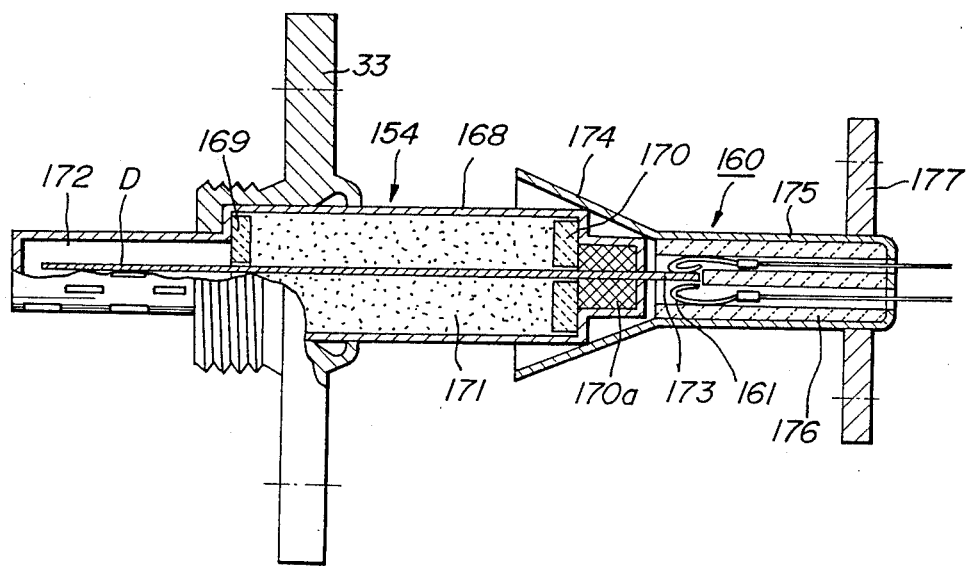

Hereinafter, more detailed construction of the detecting portion 154 and the funnel-shaped contact member 160 will be explained by referring to FIG. 31. Outer periphery of the detecting portion 154 is covered by a metallic cylindrical protecting tube 168. The oxygen sensing element S is housed in this protecting tube 168. The oxygen sensing element S is supported at its middle portion by 2 disk shaped ceramic spacers 169 and 170 arranged at a certain interval. Sealant 171, for instance, cement, talc or the like is filled in the space between the spacers 169 and 170. Furthermore, sealing agent 170a,  for instance, glass or the like is filled up to surround the oxygen sensing element S in a space between the ceramic spacer 170 and base end side of the protecting tube 168 so that these portion of the sensing element can be made air-tight against the space 172 in the top end portion of the protecting tube 168. The oxygen detecting portion D of the oxygen sensing element S is arranged to locate in the abovementioned isolated space 172. Whereas at the base end side of the oxygen sensing element S, a base portion 173 thereof having an outlet of the air passageway and an electric contact terminal M is arranged to project outwardly from the protecting tube 168.

This base portion 173 of the oxygen sensing element S projecting and extending outwardly from the protecting tube 168 is guided by an inner surface of a cone shaped portion 174 of the funnel shaped contact member 160 having a low temperature sintered ceramic housing and is coupled thereto by insertion. The insertion of this base portion 173 is limited by abutment of the housing of the protecting tube 168 against the cone shaped portion 174. Thus an excess insertion of the detecting portion 154 into the contact member 160 is effectively prevented. The inserted base portion 173 of the oxygen sensing element S is provided with the electric contact terminal M provided on the both surfaces by printing (refer to FIG. 7-B). This electric contact terminal M comes in contact with connector members 161 formed of heat resistive spring material and establishes electric connection therewith. The material of the connector members 161 may be SUS material, Ni-Cr steel or the like, which does not decrease the spring feature at the high temperature for instance 600° C. and platinum or gold plating is applied thereon for improving the conductivity. By using such materials for the connector members, the electric contact between the electric contact terminal M and the connector members 161 can be effectively maintained even the contact member 160 is exposed to high temperature atmosphere. Thus a very stable electric connection is obtained. In a cylindrical portion 175 of the contact member 160, an insulator 176 is housed for keeping mutual insulation of the connector members 161 and the platinum lead wires connected thereto.

Reference numeral 177 is a mounting flange to be secured against the projections 159 in the probe by screws. (refer to FIG. 30)

As has been explained in the foregoing, the electric connection for the plural numbers of the lead wires connected to the printed electric contact terminal M can be established at once by the inserting operation of the base portion 173 of the oxygen sensing element S. The device has a remarkable effect for the simplification and speed up of the electric connecting works in the handling of the oxygen concentration measuring devices and thus also in the assembling work thereof.

Figure 32:
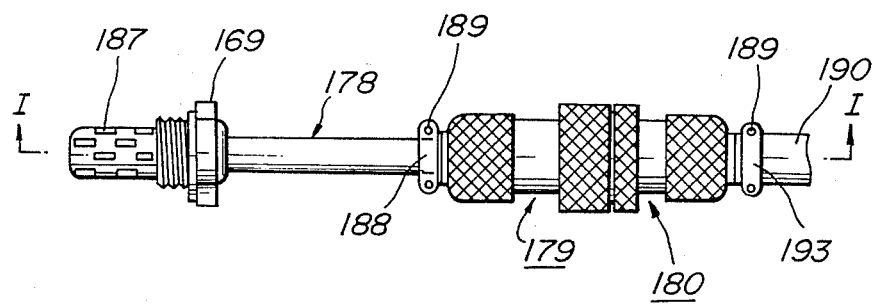

FIG. 32 shows general view of the oxygen concentration measuring device according to the present invention. In the drawing, reference numeral 178 shows a protecting tube for covering the detecting portion and the numerals 179 and 180 show connector parts coupled to the protecting tube 178.

Figure 33:
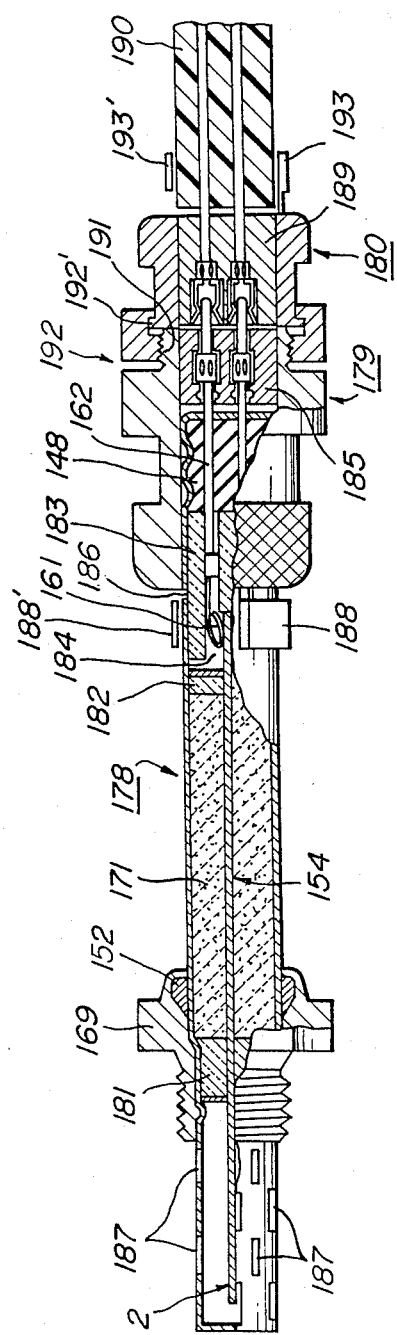

The construction of the device of the present invention will be explained also referring to FIG. 33 which shows partially in cross-section. A detecting portion 154 is essentially an oxygen sensing element S formed of narrow width elongated shaped solid electrolyte having zirconia as the main consistent of the size of about 5 mm(width)×1.5 mm(thickness)×30-60 mm(length) and at the top end thereof an oxygen detecting portion D is formed. The oxygen sensing element S is supported at two middle portions by insulators 181 and 182, and at its base end portion by an insulator 183 and is housed in a generally cylindrical protecting tube 178. The inner space of the tube 178 between the insulators 181 and 182 is filled with sealant like cement, talc, glass etc. and the inner space of the protecting tube 178 is separated in air-tight manner. In a top side space of thus isolated spaces, the oxygen detecting portion D of the oxygen sensing element is positioned. Whereas in a base end side space 184 of the protecting tube 178 (right hand side in FIG. 33), the outlet of the air passageway 51 formed in the oxygen sensing element S as shown in FIG. 8 and the electric contact terminal M are located. In this space 184, connector members 161 to be coupled with the base end portion of the oxygen sensing element S printed with the electric contact terminal M is provided in the metallic connector 179. Lead wires 162 derived from the connector members 161 are connected with male plugs 185 of the metallic connector 179 by penetrating through a rubber plug 149 being pressed in right end portion of the protecting tube 178 and fixed the position by caulking. Reference numeral 186 shows a hole for introducing the reference gas to the outlet of said air passageway. The reference gas introduced from this reference gas introducing hole 186 flows into the air passageway by diffusion and comes in contact with the reference electrode 45 exposed in the air passageway as shown in FIG. 8.

A plurality of holes 187 are formed at the top end portion of the protecting tube 178. The measuring gas is introduced through these holes 187 and the measuring electrode 44 shown in FIG. 8 in the oxygen detecting portion D exposed to the measuring gas may contact with the measuring gas.

Reference numeral 169 is a housing for securing the protecting tube 178 at the furnace wall of the combustion furnace after inserting the protecting tube through a hole. Reference numeral 152 is a metal sealing ring for keeping air tight sealing between the housing 169 and the protecting tube 178.

At the periphery of the base end portion of the protecting tube having the abovementioned construction, the metallic connector portion 179 having the male plugs to be connected with the lead wires 162 is mounted. The mounting is effected by fastening bolt and nut or the like passed through holes 189 (FIG. 32) provided on the spring members 188 and 188' coupled at one hand with the metallic connector portion 179 and separated therefrom at the other end and by causing elastic deformation of the spring members 188 and 188' and that part of the protecting tube contacting with the spring members. In this manner, the metallic connector portion 179 is held against the protecting tube 178. It is also possible to interpose asbestos between the spring members 188, 188' and the protecting tube 178 so as to further prevent dropping off the metallic connector portion from the protecting tube 178.

The male plugs 185 of the metallic connector portion 179 are to be inserted into female plug 189 of the metallic connector portion 180 to establish electric contact between the metal contact members of the male plug 185 and the female contact members of the female plugs 189. The female contact members of the female plugs 189 are connected with lead wires 190 to be connected outside controlling circuits. In the manner as explained above, the electric signal obtained from the oxygen sensing portion D is supplied to the controlling circuit at outside via the printed electric contact terminal M, connector member 161, lead wires 162, male plug 185, female plug 189 and the lead wires 190.

In order to make coupling between the male plug 185 and the female plug 189 more definite, a male thread portion 191 is provided at outer surface of the male plug of the metallic connector 179 and a female thread portion is provided in the inner surface of a metal ring 192 moving over the outer surface of the metallic connector portion 180 and by coupling the two thread portions, the metallic connector portions 179 and 180 are jointly coupled together and the electric connection therebetween becomes more definite. A projection 192' is provided on the outer surface of the metallic connector portion 180 at the male plug side end and by means of this projection dropping of the metal ring 192 is prevented and to maintain the coupling between the metallic connector portions 179 and 180.

The jointing of the lead wire 190 to the metallic connector portion 180 is effected by fastening together two spring members 193 and 193' elastically against the lead wire 190 just like as explained in the jointing of the protecting tube 178 against the metallic connector portion 179.

As has been explained in the foregoing, the oxygen concentration measuring device according to the present invention has the following advantages.

Since the detecting portion is constructed in small size and hence the thermal capacity of the same becomes very small, the time required to warm up the sensing element at a predetermined temperature by a heat source such as the heater members or the measuring gas can be made very short. Also the response time of the device is shortened since the space of the detecting portion is small. Accordingly, the warming up time counted from the star of warming by the heat source to the time able to commence the measurement is very shortened and thus the power consumption for the heating can be decreased. The response time can be made about $\frac{1}{2}$ to $\frac{1}{3}$ of that of the conventional systems.

Also by the miniaturization of the detecting portion, the diameter of the probe can be made small, for instance, in an order of about 20 mm and this affords the decrease of the total weight of the device and the easy mounting to the furnace or the like becomes possible.

When the sensing element is formed of an oxygen concentration cell and an oxygen pumping portion, the concentration of the oxygen near the measuring electrode can be controlled by the oxygen pumping portion so that a measurement over a more wider range of the oxygen concentration, more exactly, a wide range from the oxidation atmosphere to the reducing atmosphere, becomes possible.

Since the diameter of the probe can be made small, the exchange rate of the gas is improved at high response time and the amount of suction of the gas by sucking means can be made small. By sucking the measuring gas by the sucking means, the variation of the response time due to variation of the flow rate of the measuring gas can be avoided.

When arranging the sucking means outside the furnace wall, the corrosion or blocking of the gas passageway due to condensation of moisture or acid vapour may effectively be prevented by heating the temperature of the gas passageway over the dew point temperature of the measuring gas by providing heat insulating means or heating and heat insulating means in the measuring gas passageway outside the furnace.

Since the measuring gas is supplied to the detecting portion by an ejector and also this measuring gas is exhausted outwardly before its temperature comes substantially below the dew point temperature so that the measurement can be made without variation of the response time even the flow rate of the measuring gas variates.

By providing temperature compensating operation means and further the temperature controlling means, the oxygen concentration can be measured over a wide temperature range of the measuring gas, for instance, from the normal temperature to 1400° C.

The oxygen concentration measuring device according to the present invention having novel connector members has the following advantages.

The mounting and detaching of the detector portion to the probe is very easy. Since a more definite electric connection is maintained in a more high temperature atmosphere compared with the conventional devices, the connecting work of the detecting portion becomes very simple and also the assembling work is simplified.

In the oxygen concentration measuring device according to the present invention, the connection between the outside lead wires and that from the detecting portion is easy and the connection is quite definite so that the lead wires are protected from spoiling by the high temperature and misconnection may be prevented.

Since the detecting portion in general is made light weight and the size thereof is miniaturized, the small measuring chamber becomes very small and hence the amount of calibration gas to be supplied can be made very small.

Further by the decrease of space of the small measuring chamber, the calibration gas can be filled up in the small measuring chamber almost instantaneously so that the calibration can be made during the measurement. Furthermore, since the inside pressure in the small measuring chamber can be increased immediately by the supply of the calibration gas, the blow-back purge of the filter can simply be effected.

What is claimed is:

1. An industrial oxygen concentration measuring device for determining an oxygen concentration of a measurement gas, comprising:
    a detecting portion comprising a unitary body formed from a plurality of laminated plate members including an oxygen sensing element comprising an oxygen concentration cell made of solid electrolyte, a temperature detecting member and a heater; and
    a temperature operational processing unit having temperature compensation operation means for compensating a setting voltage, to which an electromotive force generated by said oxygen concentration cell is compared, for variations in temperature of said detecting portion at temperatures above 600° C., said temperature of said detecting portion being determined by an output signal obtained from said temperature detecting member.

2. An oxygen concentration measuring device according to claim 1, further comprising a probe member having a top portion which is disposed in a measurement gas, and a base portion, wherein said detecting portion is positioned in said base portion.

3. A oxygen concentration measuring device according to claim 2, further comprising a suction member disposed in proximity to said detecting portion, for introducing the measurement gas into said probe and into communication with said detecting portion.

4. An oxygen concentration measuring device according to claim 3, wherein said suction member is positioned proximate to said base portion and said base portion is positioned on an outside portion of a furnace wall, said suction member further comprising a passageway to transport the measurement gas, said passageway including a heat insulating member or a heater and a heat insulating member provided thereon.

5. An oxygen concentration measuring device according to claim 1, further comprising a probe member having a top portion which is disposed in a measurement gas and a base portion, wherein said detecting portion is positioned in said top portion.

6. An oxygen concentration measuring device according to claim 1, wherein said oxygen sensing element further comprises an oxygen pump cell.

7. An industrial oxygen concentration measuring device comprising:
    a detecting portion comprising a unitary body formed from a plurality of laminated plate members including an oxygen sensing element comprising an oxygen concentration cell made of a solid electrolyte, a temperature detecting member and a heater; and
    a temperature operational processing unit including means for controlling power supplied to said heater for heating said detecting portion when a temperature of said detecting portion is below about 600° C. and temperature compensation operation means for compensating a setting voltage, to which an electromotive force generated by said oxygen concentration cell is compared, for variations in temperature of said detecting portion at temperatures above 600° C., said temperature of said detecting portion being determined by an output signal obtained from the temperature detecting member.

8. An oxygen concentration measuring device according to claim 7, further comprising a probe member wherein said detecting portion is positioned, said probe member having a top portion which is disposed in a measurement gas and a base portion, said probe member including an ejector member for guiding the measurement gas into communication with the detecting portion and for removing the measurement gas from the probe member to prevent constituents contained in the measurement gas from condensing in the probe member.

9. An oxygen concentration measuring device according to claim 8, wherein said detecting portion includes an electrical contact terminal pattern printed thereon and said probe member includes an electrical contact terminal member having heat resistive electrical contacts, said heat resistive electrical contacts being mated, by insertion, with said electrical contact terminal pattern, said device further comprising a protective tube for detachably accommodating the detecting portion therein, such that the detecting portion can establish an electrical connection with said contact terminal member in a detachable manner.

10. An oxygen concentration measuring device according to claim 8, further comprising a protective tube for protecting lead wires attached to said detecting portion and a connecting terminal attached to the outer periphery of an end of said protective tube and in electrical communication with said lead wires.

11. An oxygen concentration measuring device according to claim 7, wherein said oxygen sensing element further comprises an oxygen pump cell.

12. An industrial oxygen concentration measuring device, comprising:
- a detecting portion comprising a unitary body formed from a plurality of laminated plate members including an oxygen sensing element comprising an oxygen concentration cell made of solid electrolyte, a temperature detecting member and a heater;
- a temperature operational processing unit having temperature compensation operation means for compensating a setting voltage, to which an electromotive force generated by said oxygen concentration cell is compared, for variations in temperature of said detecting portion at temperatures above 600° C., said variations in temperatures being determined by an output signal obtained from said temperature detecting member;
- a probe member having a top portion which is disposed in a measurement gas contained in a furnace chamber, and a base portion which is positioned on an outside portion of a furnace wall;
- a measuring chamber located proximate to said top portion, said measuring chamber being in communication with said measurement gas through a filter disposed between said measurement gas and said measuring chamber, wherein at least an oxygen detecting portion of said detecting portion is positioned in said measuring chamber; and
- a calibration gas introduction tube located in gaseous communication with said measuring chamber, for introducing a calibration gas into said measuring chamber.

13. An oxygen concentration measuring device according to claim 12, wherein said filter allows the measurement gas to penetrate into said measuring chamber by diffusion.

14. An oxygen concentration measuring device according to claim 13, wherein said filter has a diffusion resistance to gas flow such that the pressure in the measuring chamber increases when the calibration gas is introduced into said measuring chamber.

15. An oxygen concentration measuring device according to claim 12, wherein said oxygen sensing element further comprises an oxygen pump cell.

* * * * *